US006844183B2

(12) United States Patent
Kimura et al.

(10) Patent No.: US 6,844,183 B2
(45) Date of Patent: Jan. 18, 2005

(54) ANTIBIOTICS RK-1061 AND PROCESS FOR PREPARING THE SAME

(75) Inventors: Ken-ichi Kimura, Utsunomiya (JP); Yoshikazu Ikeda, Shimotsuga-gun (JP); Shinobu Kagami, Shimotsuga-gun (JP); Hidetoshi Takahashi, Kawachi-gun (JP); Kousaku Takahashi, Utsunomiya (JP); Makoto Yoshihama, Utsunomiya (JP); Makoto Ubutaka, Imizu-gun (JP); Kiyoshi Isono, Oomiya (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 191 days.

(21) Appl. No.: 10/212,519

(22) Filed: Aug. 5, 2002

(65) Prior Publication Data

US 2003/0050471 A1 Mar. 13, 2003

Related U.S. Application Data

(62) Division of application No. 09/171,787, filed as application No. PCT/JP97/01466 on Apr. 25, 1997, now Pat. No. 6,455,694.

(30) Foreign Application Priority Data

Apr. 26, 1996 (JP) .............................. 8-131444

(51) Int. Cl.$^7$ ................................ C12N 1/20
(52) U.S. Cl. ................................... 435/253.5
(58) Field of Search ..................... 435/253.5, 252.35

(56) References Cited

FOREIGN PATENT DOCUMENTS

| JP | 61-282088 | 12/1986 |
|---|---|---|
| JP | 2-306992 | 12/1990 |

OTHER PUBLICATIONS

Isono, et al., "Liposidomycins: Novel Nucleoside Antibiotics Which Inhibit Bacterial Peptidoglycan Synthesis." *The Journal of Antibiotics* XXXVIII (11): 1617–1621 (Nov., 1985).
Izaki, et al., "Biosynthesis of the Peptidoglycan of Bacterial Cell Walls." *The Journal of Biological Chemistry* 243 (10): 3179–3192 (May 25, 1968).
Inukai, et al., "Mureidomycins A–D, Novel Peptidylnucleoside Antibiotics With Spheroplast Forming Activity. I. Taxonomy, Fermentation, Isolation and Physico–Chemical Properties." *The Journal of Antibiotics* 42: 662–679 (1989).

Knapp, et al., "Synthesis of the Liposidomycin Diazepanone" *Tetrahedron Letters* 33(38): 5485–5486 (1992).
Ubukaka, et al., "Structure Elucidation of Liposidomycins, a Class of Complex Lipid Nucleoside Antibiotics" *J. Org. Chem.* 57(24): 6392–6403 (1992).
Kimura, et al., "Liposidomycin C Inhibits Phospho–N–acetylmuramyl–pentapeptide Transeferase in Peptidoglycan Synthesis of *Escherichia coli* Y–10" *Agric. Biol. Chem.* 53(7): 1811–1815 (1989).
Ubukata, "Chemical Studies on Novel Antibiotics (in Japanese)" *Journal of the Agricultural Chemical Soc. of Japan* 62(11): 1629–1636 (1988).
"Microbiological Industry (in Japanese)" K.K. Asakura Shoten 609–620 (1956).
Ubukaka, "Chemical Studies on Novel Antibiotics (in Japanese)" *Journal of the Agricultural Chemical Soc. of Japan* 62(11): 1629–1636 (1988), and English language translation thereof.
"Microbiological Industry (in Japanese)" K.K. Asakura Shoten, pp. 609–620 (1956), and English language translation thereof.

*Primary Examiner*—Sandra E. Saucier
(74) *Attorney, Agent, or Firm*—Testa Hurwitz & Thibeault LLP

(57) ABSTRACT

Antibiotics RK-1061s having a novel chemical structure and a method of production thereof.

They have a structural formula represented by general formula(I) wherein A represents $R_1$ or $R_1CH(OR_2)CH_2$. $R_2$ represents 3-methylglutaric acid residue and $R_3$ represents a sulfate group or a hydrogen atom. The process comprises culturing a ray fungus belonging to the genus *Streptomyces* and isolating RK-1061s from the culture. *Streptomyces* sp. SN-1061Ms (FERM BP-5800) is capable of stably producing RK-1061 at a high productivity.

1 Claim, 21 Drawing Sheets

ANTIBIOTICS RK-1061 AND PROCESS FOR PREPARING THE SAME

This is a division of U.S. application Ser. No. 09/171,787, filed on Jan. 12, 1999, now U.S. Pat. No. 6,455,694 which is a 35 U.S.C. § 371 application of PCT/JP97/01466, filed Apr. 25, 1997 the entire disclosures of which are incorporated by reference herein.

TECHNICAL FIELD

The present invention relates to a novel antibiotic RK-1061s named as liposidomycins and pharmacologically acceptable salts thereof and a method of producing them.

PRIOR ART

In the case of development of a highly specific antibacterial agent with little side-effects, an agent which can target a specific site present in bacteria of prokaryotes but absent in human of eukaryotes is desired. As such a specific site, peptidoglycan which is one of bacterial cell wall components can be exemplified and penicillins, cephems, carbapenems, monobactams, cycloserine, bacitracin, vancomycin, phosphomycin are known as launched antibiotics which act on peptidoglycan.

DISCLOSURE OF THE INVENTION

It is well known that any excellent antibiotic will induce resistant bacteria by using it for a long time. In addition, some antibiotics have side-effects such as neuropathy, nephropathy and/or hepatopathy. Recently, infection of MRSA (Methicillin resistant *staphylococcus aureus*) in a hospital and *Helicobacter pylori* which is thought to play a role as a cause of gastric ulcer and/or gastric cancer become the topics in the field. From these points of view, development of an antibiotic having a novel structure and action mechanism is desired. Antibiotic liposidomycins (RK-1061s) were found by using screening system of inhibiting peptidoglycan synthesis. This antibiotic has an action of specifically inhibiting phospho-N-acetylmuramyl-pentapeptide transferase (E. C. 2. 7. 8. 13)(Phospho-MurNAc-pentapeptide translocase, UDP-MurNAc-pentapeptide phosphotransferase, (common name) translocase I) (Agri. Biol. Chem., 53(7), 1811–1815 (1989)) and structural characteristic of being a fatty acyl nucleoside antibiotic with sulfate group and unique aminosugar group. Though Tunicamycin ("Tunicamycin", Japan Scientific Societies Press, 1982, Tokyo) and Mureidomycin (J. Antibiot., 42, 662–679 (1989)) are known to have the same action as liposidomycins, according to the above references, liposidomycins has an antibacterial spectrum different from those of the other two antibiotics and powerful inhibitory activity thereof on peptidoglycan synthesis. Therefore, liposidomycin theoretically has a possibility of being effective against the all bacteria having peptidoglycan if it has not problem on permeability or stability.

Liposidomycins has a potent antibacterial activity especially on *Mycobacterium* belonging to acid-fast bacteria (J. Antibiot., 38, 1617–1621 (1985)) and is expected to be effective against *Mycobacterium tuberculosis* resistant to known anti-tuberculotic agent such as rifanpicin etc. against which any agent is not effective. Further, opportunistic infectious disease such as pneumocystis carinii becomes serious problem according to the explosive increase in the number of patient with AIDS and liposidomycins can be expected to be effective against adventitious anti-fast bacterium *Mycobacterium avium* complex (MAC) which causes the aforementioned opportunistic infectious disease.

The present inventors investigated to produce high yield of RK-1061s which are antibiotics composed of many components and to isolate novel components therefrom and found novel substances different from RK-1061A (liposidomycins A), RK-1061B (liposidomycins B), RK-1061C (liposidomycin C) (Japanese unexamined patent application No. 282088/1986), RK-1061G (liposidomycins G), RK-1061H (liposidomycins H) (Japanese unexamined patent application No. 306992/1990) which were already reported. Though the all reported substances can be classified into general formula (II) as will be described below, liposidomycins obtained by the present invention are novel compounds which have a structure with novel group at $R_1$ group of formula (II) and can be classified into 3 different types which belong to structure (III), (IV) and (V). Further, novel antibiotic liposidomycins (RK-1061s) obtained by the present invention, especially compounds without sulfate group having structure (IV) or (V), demonstrated significantly higher antibacterial activity than the other compounds. Then, the present invention was accomplished.

An object of the present invention is to provide novel antibiotic liposidomycins (RK-1061s), highly productive cell lines thereof and a method of producing them.

The present invention relates to liposidomycins (RK-1061s) represented in the following general formula (I) or pharmacologically acceptable salts thereof.

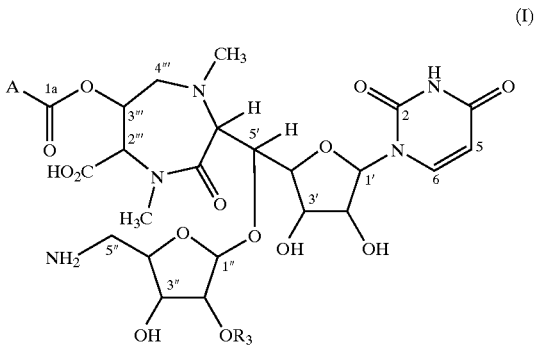

(I)

A in the formula represents $R_1$ or $R_1CH(OR_2)CH_2$.

$R_2$ represents 3-methylglutaric acid residue(—CO—$CH_2$—CH($CH_3$)—$CH_2$—COOH), $R_3$ represents hydrogen atom (H) or sulfate group($SO_3H$). Further, in the case of $R_1CH(OR_2)CH_2$, $R_1$ represents $C_nH_{2n+1}$ (n represents an integer between 1–20), $C_nH_{2n-1}$ (n represents an integer between 2–21) or $C_nH_{2n-3}$ (n represents an integer between 3–22). And in the case of $R_1$, $R_1$ represents $C_nH_{2n-1}$ (n represents an integer between 2–21), $C_nH_{2n-3}$ (n represents an integer between 3–22) or $C_nH_{2n-5}$ (n represents an integer between 4–23).

As for the compounds, liposidomycins represented in the following formula (II)–(V) can be exemplified.

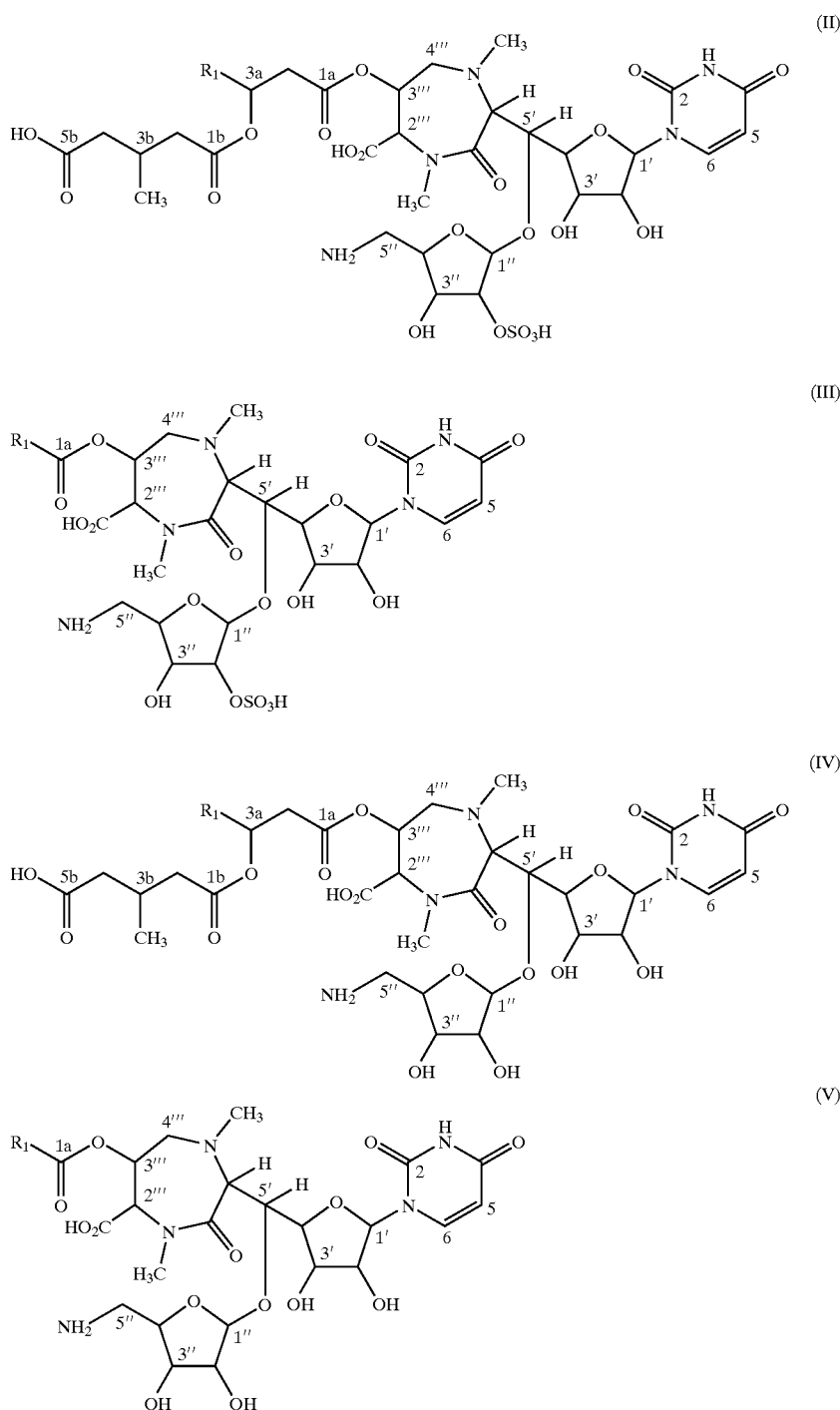

R₁ represents the same as described before.

According to species of substituted group A and R₃, liposidomycins RK-1061s of the present invention can be classified into the following types. That is, they can be classified into 2 types, that is, one type in which A is $R_1CH(OR_2)CH_2$ (wherein $R_2$ is 3-methylglutaric acid residue) and another type in which A is $R_1$ (wherein $R_2$ is not present, $R_1$ directly binds to 2a position). And also they can be classified as $R_3$ is sulfate group and hydrogen atom.

| | Substituent | | Structural |
|---|---|---|---|
| | $R_2$ | $R_3$ | Formula |
| Type I | 3-methylglutaric acid | sulfate group | Formula II |
| Type II | direct bonding | sulfate group | Formula III |
| Type III | 3-methylglutaric acid | hydrogen atom | Formula IV |
| Type IV | direct bonding | hydrogen atom | Formula V |

As a pharmacologically acceptable salt of these RK-1061s of the present invention, hydrochloride, sulfate, alkaline metal salt such as sodium or potassium etc., alkaline earth metal salt such as magnesium or calcium etc. other metal salt such as aluminium etc. and organic amine salt such as alkyl amine salt or pyridinium salt can be exemplified.

Further, the present invention relates to a method of producing liposidomycins (RK-1061s) represented as the above formula.

That is, the producing method of the present invention is a method of producing liposidomycins (RK-1061s) comprising the following steps:

1) culturing microorganism which belongs to *Streptomyces* and which has a capability to produce the aforementioned liposidomycins (RK-1061s) in culture medium;
2) producing said liposidomycins (RK-1061s); and
3) collecting said liposidomycins (RK-1061s) from the cultured products.

These compounds of the present invention can be isolated by utilizing the difference of retention time of each compound by HPLC etc.

In addition, these compounds such as liposidomycins (RK-1061) whose $R_3$ is sulfate group or hydrogen atom can be selectively produced by selecting carbon source of culture medium. For example, liposidomycins (RK-1061s) with R3 of sulfate group can be highly produced using glucose or maltose as carbon source, while liposidomycins (RK-1061s) with $R_3$ of hydrogen atom can be highly produced using at least one carbon source selected from the group consisting of xylose, lactose, D-fructose, sucrose, inositol and D-mannitol and wheat germ or malt extract as nitrogen source.

As actinomycetes producing liposidomycins (RK-1061s) of the present invention, soil bacterium *Streptomyces* sp. RK-1061 (hereinafter referred to RK-1061 cell line) found in soil at Misaka-cho, Yamanashi prefecture by the present inventors can be exemplified. This cell line was deposited at National Institute of Bioscience and Human Technology Agency of Industrial Science and Technology Ministry of International Trade and Industry with deposit number of FERM P-8278. A patent application claimed this FERM P-8278 cell line was already registered as Patent number JP1902732 on 8th Feb. 1995, so that those cell line can be available to public by proper procedure.

In addition, artificially mutated *Streptomyces* sp. SN-1061M (hereinafter referred to SN-1061M cell line) which was made by UV irradiation of RK-1061 cell line in order to improve its low productivity and unsuitability can be exemplified. This cell line was deposited at National Institute of Bioscience and Human Technology Agency of Industrial Science and Technology Ministry of International Trade and Industry with deposit number of FERM BP-5800.

BEST MODE OF PREFERRED EMBODIMENTS FOR PRACTICE OF THE INVENTION

[Microorganism Used in the Invention]

Figure 1:
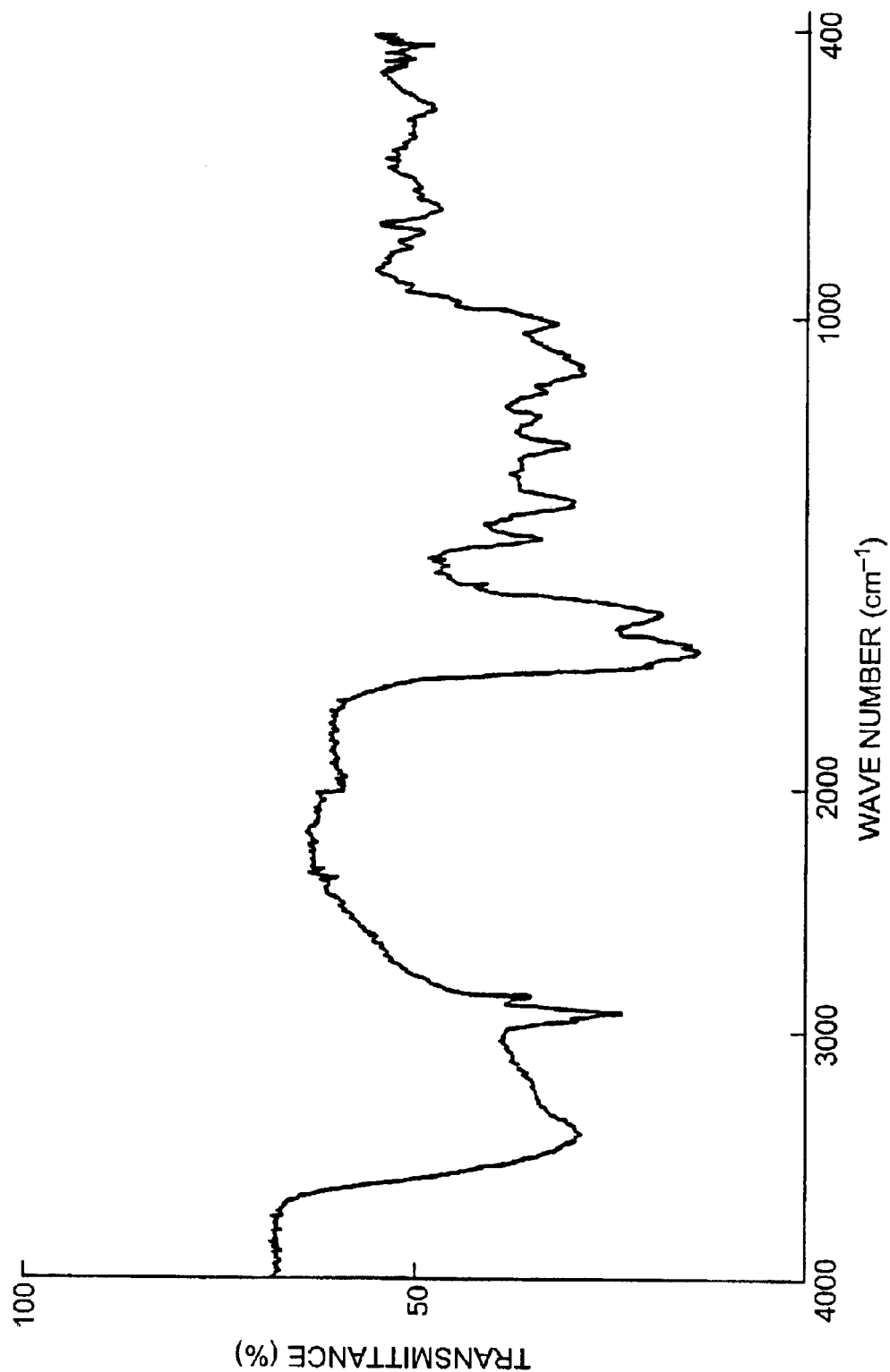
FIG. 1 demonstrates infrared absorption spectrum (KBR) of liposidomycins Z-(III).

First of all, microorganisms used in the present invention will be described below. The microorganisms used in the present invention belong to *Streptomyces* sp. and actinomycetes producing liposidomycins (RK-1061s). As an example, the aforementioned RK-1061 cell line can be exemplified. This microorganism has the above features, can produce antibiotic liposidomycins of the present invention and can be used effectively for a method of the present invention.

Not only native and artificially mutated cell lines of the above RK-1061-but-also any bacteria-belonging to *Streptomyces* sp. and producing antibiotic liposidomycins can be used in the present invention. Especially, SN-1061M cell line mutated by UV-irradiation of RK-1061 cell line in order to improve productivity of liposidomycins is more useful microorganism. The aforementioned RK-1061s were collected by a usual method of isolating soil bacteria from soil at Misaka-cho, Yamanashi Prefecture. Micobial properties of this bacterial cell line will be described below. The microbial properties thereof was already described in publication of Japanese unexamined patent application Nos. 282088/1986 and 306992/1990 and known to public.

1) Morphological Properties

RK-1061 cell line belongs to actinomycetes isolated from soil collected at Misaka-cho, Yamanashi Prefecture. Only LL-diaminopimelic acid was detected in hydrochloric acid hydrolysate of the whole cell and meso-diaminopimelic acid was not detected therein. As the results of growth tests thereof in various agar culture media, it grew in the all ten kinds of culture media. It grew well and insertion of aerial hypha and spore was prevalent only in starch-yeast extract agar culture medium, while, in other agar culture media, insertion of aerial hypha and spore was not good. In a consumption test using 11 kinds of saccharide as carbon sources, RK-1061 cell line consumed the all saccharides and grew. The aerial hypha of the present cell line was greyish and backside thereof was light brownish, which is not so special. When it grew in defatted milk, firstly aggregation occurred but peptonization occurred later to give light brown transparent solution. It hydrolyzed starch but not gelatin. Production melanin pigment was observed in culture thereof using peptone/yeast extract/iron agar culture medium and tyrosine agar culture medium but the color of soluble pigment was light brown or grey without any special pigment production. According to observations by an electron microscope, aerial hypha thereof was rectiflexible. And 3–5 rolls of dense spiral hypha was observed in oat meal/nitrate agar culture medium, while open spiral hypha was observed in potato extract/yeast extract/nitrate agar culture medium. On the other hand, any spiral hypha was not observed in the case of yeast extract agar culture medium or malt extract agar culture medium. Spores of the present bacterium were formed in lines from the end of hypha and spiral hypha was sporulated. The surface of spore was smooth but furrowed. The length of spore was 0.5–1.0 µm the width thereof was 0.5–0.7 µm. Sporangia and motile spore were not observed.

2) Growing States in Various Kinds of Culture Media (27° C., 3 Weeks)

a) Sucrose/nitrate agar culture medium
   Growth: moderate
   Aerial mycelium: none
   Reverse: 2ba (pearl)
   Soluble pigment: none
b) Glucose/asparagine agar culture medium
   Growth: moderate
   Aerial mycelium: none
   Reverse: 2ba (pearl)
   Soluble pigment:none
c) Glycerol/asparagine agar culture medium
   Growth: moderate
   Aerial mycelium: none
   Reverse: 2ba (pearl)
   Soluble pigment: none
d) Starch/inorganic salt agar culture medium
   Growth: good
   Aerial mycelium: none
   Reverse: 2ba (pearl)
   Soluble pigment: none
e) Tyrosine agar culture medium
   Growth: moderate
   Aerial mycelium: scant of b+3ni+4ni (oyster white+cobalt brown+chestnut brown)
   Reverse: 3pn (dark brown)
   Soluble pigmet: 3pl (deep brown)
f) Nutrient agar culture medium
   Growth: poor
   Aerial mycelium: none
   Reverse: 3ng (yellow maple)
   Soluble pigment: 3ng (yellow maple)
g) Yeast extract/malt extract agar culture medium
   Growth: moderate
   Aerial mycelium: excellent/e(gray)
   Reverse: 3pi (gold brown)
   Soluble pigment: 3pn (dark brown)
h) Oatmeal agar culture medium
   Growth: moderate
   Aerial mycelium: moderate 5ge (rose wood)
   Reverse: 4ge (rose beige)
   Soluble pigment: none
i) Peptone/yeast extract/iron agar culture medium
   Growth: poor
   Aerial mycelium: none
   Reverse: 2ba (pearl)
   Soluble pigment: 5pn (dark brown)
j) Starch/yeast extract agar culture medium
   Growth: good
   Aerial mycelium: excellent 4ge+4li (rose beige+beaver)
   Reverse: 4ge (rose beige)
   Soluble pigment: 1ih (olive gray)

Color code was described according to the 4th edition of Descriptive color names dictionary.

3) Efficiency of Various Kinds of Carbon Source (Pridham/Gottlieb Agar Culture Medium, 27° C. Culture)

|  | growing state |
|---|---|
| L-arabinose | ++ |
| D-xylose | +++ |
| D-glucose | ++ |
| D-fructose | + |
| sucrose | + |
| inositol | + |
| L-rhamnose | + |
| raffinose | + |
| D-mannitol | + |
| lactose | +++ |
| melibiose | ++ |

+: poor utilization
++: moderate utilization
+++: good utilization

4) Other Physiological Properties(27° C. Culture)

1. Liquefaction of gelatin (Glucose/peptone/gelatin culture medium) no liquefaction
2. Hydrolysis of starch (starch/inorganic salt agar culture medium) hydrolyzed
3. Aggregation of defatted milk and peptonization aggregates and peptonized
4. production of melanin pigment pigment production in tyrosine agar culture medium and in peptone/yeast extract/iron agar culture medium
5. Growth temperature: 20–35° C.

Streptomyces sp. having the above properties such as greyish spiral hypha, producing melanoid pigment, spore with smooth surface, consuming the aforementioned saccharides was investigated by concerning with Bergey's Manual of Determinative Bacteriology, 8th edition. As the results, the present bacterium is inferred as *Streptomyces griseosporeus* or a species very close thereto.

An example of mutating method to obtain *Streptomyces* sp. SN-1061M (FERM BP-5800) having a capability to produce a large amount of antibiotic RK-1061s of the present invention and salts thereof will be described below.

From starch/yeast extract agar culture medium slant wherein *Streptomyces* sp. RK-1061 (FERM P-8278) producing antibiotic RK-1061s and salts thereof of the present invention grew, spore was collected in 10 ml physiological saline solution and was spread in dishes so as to be $1 \times 10^8$ cells/ml. Under the conditions for about 1% of cells to grow, mutation thereof was carried out by UV irradiation and grown colonies were inoculated on the same culture media slant. From 66 cell lines cultured in K1 culture medium (culture medium comprising 40 g of sucrose (Wako-junyaku), 30 g of soy bean powder (Honen-seiyu), 20 g of wheat germ (Sigma) or 20 g of malt extract (Difco), 6 g of sodium chloride (Wako-junyaku), adjusted at pH 7.0, one cell line having a high antibacterial activity against *Mycobacterium phlei* was selected and named as *Streptomyces* sp. SN-1061M(FERM BP-5800).

1) Morphological Properties

As the results of growth tests of *Streptomyces* sp. SN-1061M in various kinds of agar culture medium, it grew in the all media. In consuming tests using 10 kinds of saccharide, it consumed the all saccharides and grew except L-rhamnose with not good consumption. The aerial hypha was whitish and back surface was light brownish, which was not so special. In defatted milk, aggregation did not occur and light brown transparent-solution was obtained after later peptonization thereof. Neither hydrolysis of starch or liquefaction of gelatin thereby was observed. Melanin pigment production was observed in yeast extract/malt extract culture medium (ISP No. 2), peptone/yeast extract/iron agar culture medium (ISP No. 6) and tyrosine agar culture medium but soluble pigment was light brown or brown, which was not so special. According to the observations by an electron microscope, the aerial hypha was linear and soft and 6–10 rolls of dense spiral hypha were in starch/yeast agar culture medium. The spores of the present bacterium were formed in lines from the end of the hypha and spiral hypha was sporulated. Spore surface was smooth but furrowed. The length of spore was 0.6–1.2 µm, width thereof was 0.6–0.7 µm. Sporangia and motile spore were not observed.

2) Growing States in Various Kinds of Culture Medium (27° C., 3 Weeks)

| Culture medium | Growth | Aerial hypha | Basal hypha | Soluble pigment |
|---|---|---|---|---|
| Starch/yeast extract | Normal | Normal, White | Light brown, 10 YR 7/4 | None |
| ISP No. 2 | Good | Normal, White | Brown, 5 YR 4/4 | Light brown 10 YR 7/6 |
| ISP No. 3 | Good | Normal, White | Light yellow, 2.5 Y 8/8 | None |
| ISP No. 4 | Good | Small amount, White | Light brown, 2.5 Y 8/4 | None |
| ISP No. 5 | Good | Normal, White | Light yellow, 5 Y 9/4 | None |
| ISP No. 6 | Normal | None | Dark brown, 10 YR 2/2 | Dark brown, 10 YR 3/2 |
| ISP No. 7 | Good | Normal, White | Light brown, 10 YR 7/4 | Light brown, 2.5 Y 8/4 |
| ISP No. 8 | Normal | None | Light yellow, 5 Y 9/4 | None |

Description of color was according to color code (gloss plate) of Japanese standard association 3) Utilization of Various Kinds of Carbon Source (ISP No. 9, 27° C., 3 Weeks)

| Carbon source | Growing state |
|---|---|
| L-arabinose | normal |
| D-xylose | good |
| D-glucose | good |
| D-fructose | good |
| sucrose | good |
| inositol | good |
| L-rhamnose | not good |
| raffinose | normal |
| D-mannitol | good |
| galactose | good |

4) Other Physiological Properties
1. Liquefaction of gelatin (Glucose/peptone/gelatin culture medium) no liquefaction
2. Hydrolysis of starch not hydrolyzed
3. Aggregation of defatted milk and peptonization no aggregation and peptonized
4. production of melanin pigment pigment production in ISP No. 2,6 and 7 culture medium
5. Growth temperature: 27–37° C.

Comparative data of activities of *Streptomyces* sp. RK-1061 and *Streptomyces* sp. SN-1061M in K1 culture medium by flask culture were shown below. Comparing antibacterial activities against *Mycobacterium phlei* of culture supernatant and extract of mycelium thereof on day 5 and 7 of culture, antibacterial activities were recognized in the case of SN-1061M and not recognized at all in the case of RK-1061. Accordingly, *Streptomyces* sp. SN-1061M was more useful cell line producing RK-1061 substances stability and in high yield amount than *Streptomyces* sp. RK-1061.

| | Streptomyces sp. RK-1061 (parent cell line) | | | | Streptomyces sp. SN-1061 M (mutated cell line) | | | |
|---|---|---|---|---|---|---|---|---|
| Culture | Amount of mycelium | | diameter of the inhibition zone (mm) | | Amount of Mycelium | | diameter of the inhibition zone (mm) | |
| days | (%) | pH | B | M | (%) | pH | B | M |
| 3 days | 33 | 7.8 | 0 | 0 | 48 | 6.1 | 0 | 0 |
| 5 days | 44 | 7.2 | 0 | 0 | 71 | 5.1 | 0 | 14 |
| 7 days | 29 | 8.0 | 0 | 0 | 67 | 5.5 | 15 | 25 |

(B: culture supernatant, M: acetone extract of mycelin)

[Method of Fermentation and Purification]

Then, the method of fermentation of bacterial cell line of the present invention belonging to *Streptomyces* sp. and producing liposidomycins and the method of isolation and purification of liposidomycins obtained by culture will be described as below. In order to obtain antibiotic liposidomycins (RK-1061s) of the present invention, the above antibiotic producing bacteria belonging to *Streptomyces* sp. can be cultured by a usual method of producing antibiotics. Liquid culture or solid culture can be used. For culture in a industrial scale, spore suspension or culture media of the above bacteria can be inoculated and cultured by aeration and stirring.

Nutritional source of culture media is not restricted specifically and carbon source, nitrogen source and others used usually in microbial culture can be comprised in culture media. As carbon source, starch, dextrin, glycerin, glucose, maltose, xylose, lactose, D-fructose, sucrose, inositol, L-rhamnose, L-arabinose, D-mannitol, raffinose, salicin, L-sorbose and/or D-glucosamine can be used and, as nitrogen source, wheat germ, malt extract, peptone, soy bean powder, meat extract, rice bran, wheat bran, urea, corn steep liquer, ammonium salt, nitrate, other organic and/or inorganic nitrogen compounds can be used. In addition, inorganic salts such as table salt, phosphate, metal salts including sodium, potassium, zinc, manganese, iron etc. can be added thereto. and, if necessary, animal oil, plant oil and/or mineral oil can be added as an anti-foaming agent. Culture conditions such as culture temperature, culture duration time, etc. can be selected in order to obtain appropriate bacterial growth and maximum production of liposidomycins. For example, suitable pH of culture medium is 4–9, preferably 6–7 and suitable culture temperature is preferably 25–35° C. And it is a matter of course that these culture conditions such as culture compositions, pH of culture medium, culture temperature, stirring conditions should be adjusted depending on species of bacterial cell line used, surrounding conditions etc. in order to obtain preferable results.

Further, as described before, if specific carbon source is used, substance with $R_3$ of sulfate group or hydrogen atom can be selectively produced. To obtain liposidomycins from culture products, means used usually to obtain metabolic products can be appropriately used. For example, one or combination of means to utilize the difference between solubility, adsorption affinity, molecular weight etc. of liposidomycins and those of contaminants can be used at single time or repeatedly.

More specifically, liposidomycins are present in both of culture filtrate and mycelium body and active fraction present in mycelium can be obtained by extraction with acetone including water and evaporation of acetone thereafter. After combining this with the above culture filtrate, liposidomycins can be obtained by purification such as solvent extract, silicagel chromatography, gel filtration chromatography etc. As a solvent for solvent extract, butanol is suitable and Sephadex LH-20 is suitable for gel filtration chromatography. Obtained RK-1061s are separated into many component peaks by high performance liquid chromatography. A column of reversed-phase distribution type is advantageously used. Each fraction corresponding to each liposidomycins can be collected, condensed, desalted and freeze-dried to yield pure liposidomycins.

[Physicochemical Properties]

The liposidomycins (RK-1061s) of the present invention have the following physicochemical properties:

(1) Appearance: white powder (the all components)
(2) Molecular weight and molecular formula: Molecular weight determined by mass spectrometry (FAB-MS) and high resolution mass spectrometry (HRFAB-MS) and molecular formula are represented in Table 1.

TABLE 1

| compound | molecular formula | $R_1$ | molecular weight |
|---|---|---|---|
| (I) Type I (having both sulfate group and 3-methylglutaric acid residue) | | | |
| 1. Z: | $C_{42}H_{65}N_5O_{21}S$ | $C_{11}H_{21}$ | 1007 |
| 2. L: | $C_{44}H_{71}N_5O_{21}S$ | $C_{13}H_{27}$ | 1037 |
| 3. M: | $C_{44}H_{71}N_5O_{21}S$ | $C_{13}H_{27}$ | 1037 |
| 4. K: | $C_{46}H_{71}N_5O_{21}S$ | $C_{15}H_{27}$ | 1061 |
| 5. N: | $C_{46}H_{73}N_5O_{21}S$ | $C_{15}H_{29}$ | 1063 |
| (II) Type II (having sulfate group but not 3-methylglutaric acid residue) | | | |
| 1. A-(II): | $C_{38}H_{57}N_5O_{17}S$ | $C_{15}H_{25}$ | 887 |
| 2. C-(II): | $C_{36}H_{57}N_5O_{17}S$ | $C_{13}H_{25}$ | 863 |
| (III) Type III (having not sulfate group but 3-methylglutaric acid residue) | | | |
| 1. X-(III): | $C_{41}H_{65}N_5O_{18}$ | $C_{10}H_{21}$ | 915 |
| 2. Y-(III): | $C_{42}H_{63}N_5O_{18}$ | $C_{11}H_{19}$ | 925 |
| 3. Z-(III): | $C_{42}H_{65}N_5O_{18}$ | $C_{11}H_{21}$ | 927 |
| 4. C-(III): | $C_{42}H_{67}N_5O_{18}$ | $C_{11}H_{23}$ | 929 |
| 5. V-(III): | $C_{44}H_{65}N_5O_{18}$ | $C_{13}H_{21}$ | 951 |
| 6. A-(III): | $C_{44}H_{67}N_5O_{18}$ | $C_{13}H_{23}$ | 953 |
| 7. G-(III): | $C_{44}H_{69}N_5O_{18}$ | $C_{13}H_{25}$ | 955 |
| 8. M-(III): | $C_{44}H_{71}N_5O_{18}$ | $C_{13}H_{27}$ | 957 |
| 9. K-(III): | $C_{46}H_{71}N_5O_{18}$ | $C_{15}H_{27}$ | 981 |
| 10. N-(III): | $C_{46}H_{73}N_5O_{18}$ | $C_{15}H_{29}$ | 983 |
| (IV) Type IV (having neither sulfate group or 3-methylglutaric acid residue) | | | |
| 1. A-(IV): | $C_{38}H_{57}N_5O_{14}$ | $C_{15}H_{25}$ | 807 |
| 2. C-(II): | $C_{36}H_{57}N_5O_{14}$ | $C_{13}H_{25}$ | 783 |

(3) Melting point: Each component does not have clear melting point and decomposes at 150–250° C.
(4) Specific rotation power Liposidomycins A-(III): $[\alpha]_D^{24} = +22°$ (c 0.1, 50% methanol)

Liposidomycins Z-(III): $[\alpha]_D^{24} = +20°$ (c 0.1, 50% methanol)

Figure 2:
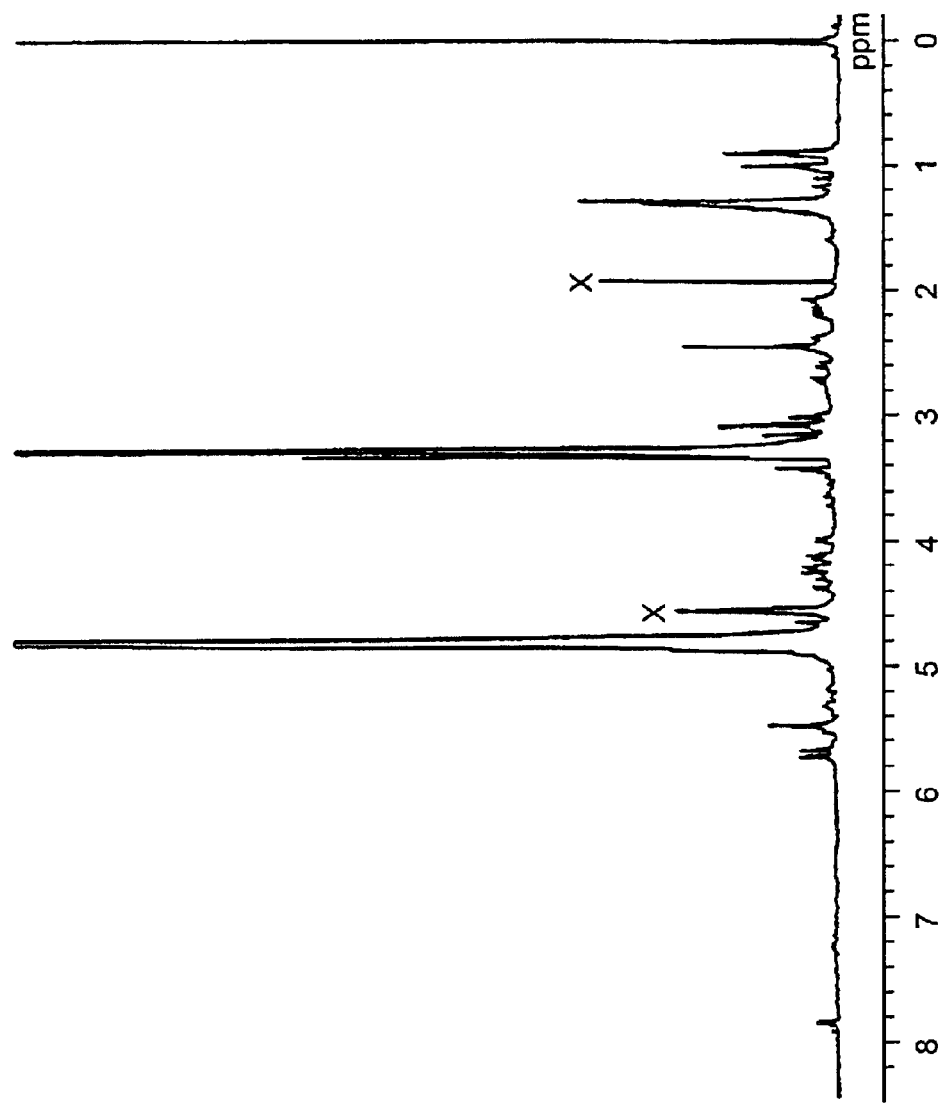
FIG. 2 demonstrates $^1$H-NMR spectrum (500 MHz, CD$_3$OD) of liposidomycins Z and x represents peaks unrelated to the substance of the present invention.
Figure 3:
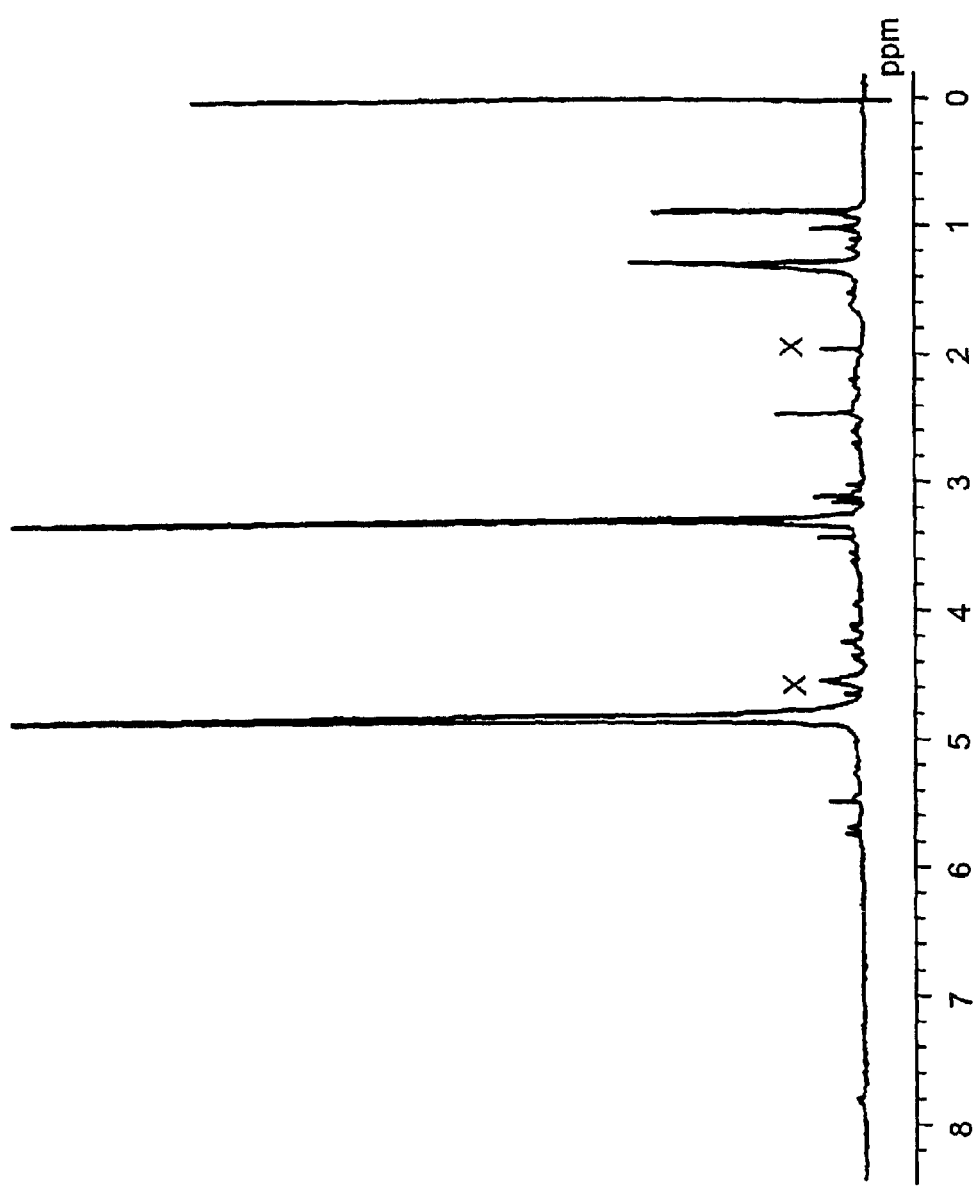
FIG. 3 demonstrates $^1$H-NMR spectrum (500 MHz, CD$_3$OD) of liposidomycins L and x represents peaks unrelated to the substance of the present invention.
Figure 4:
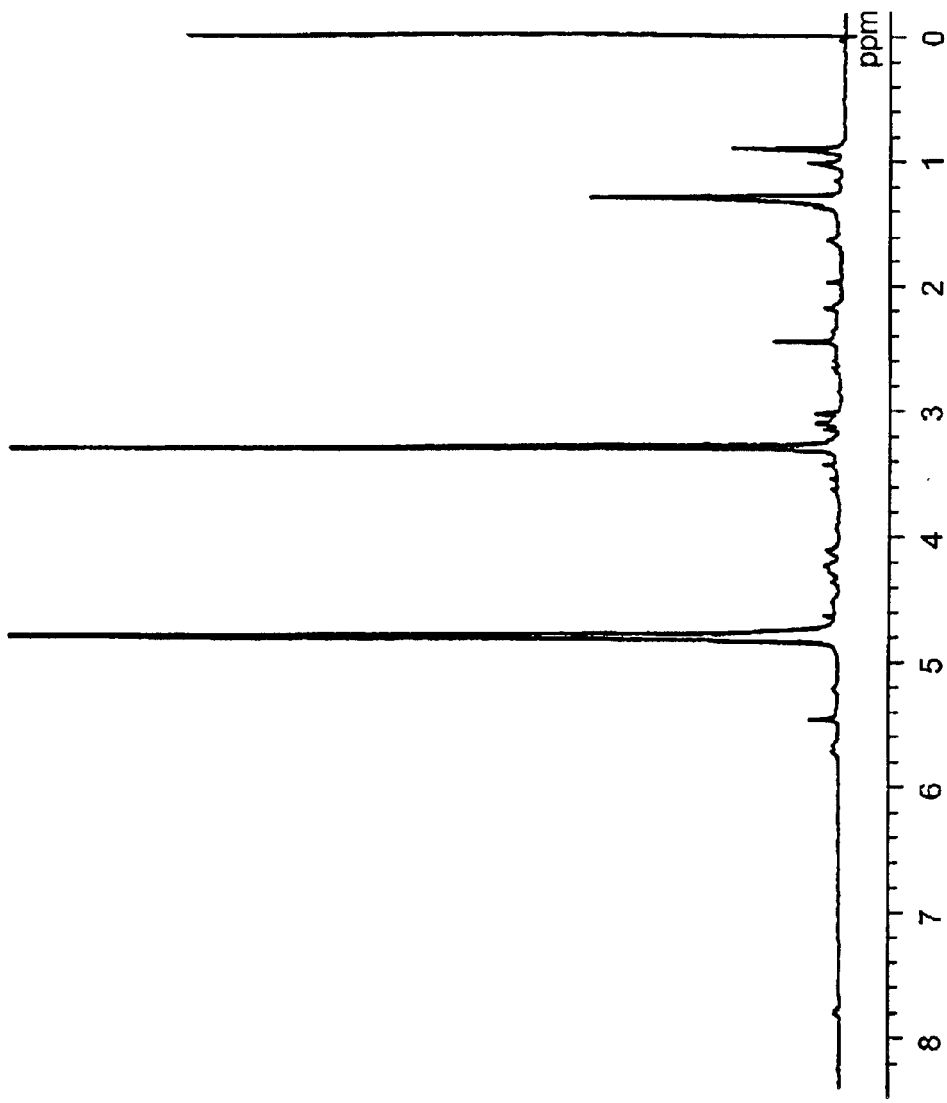
FIG. 4 demonstrates $^1$H-NMR spectrum (500 MHz, CD$_3$OD) of liposidomycins M.
Figure 5:
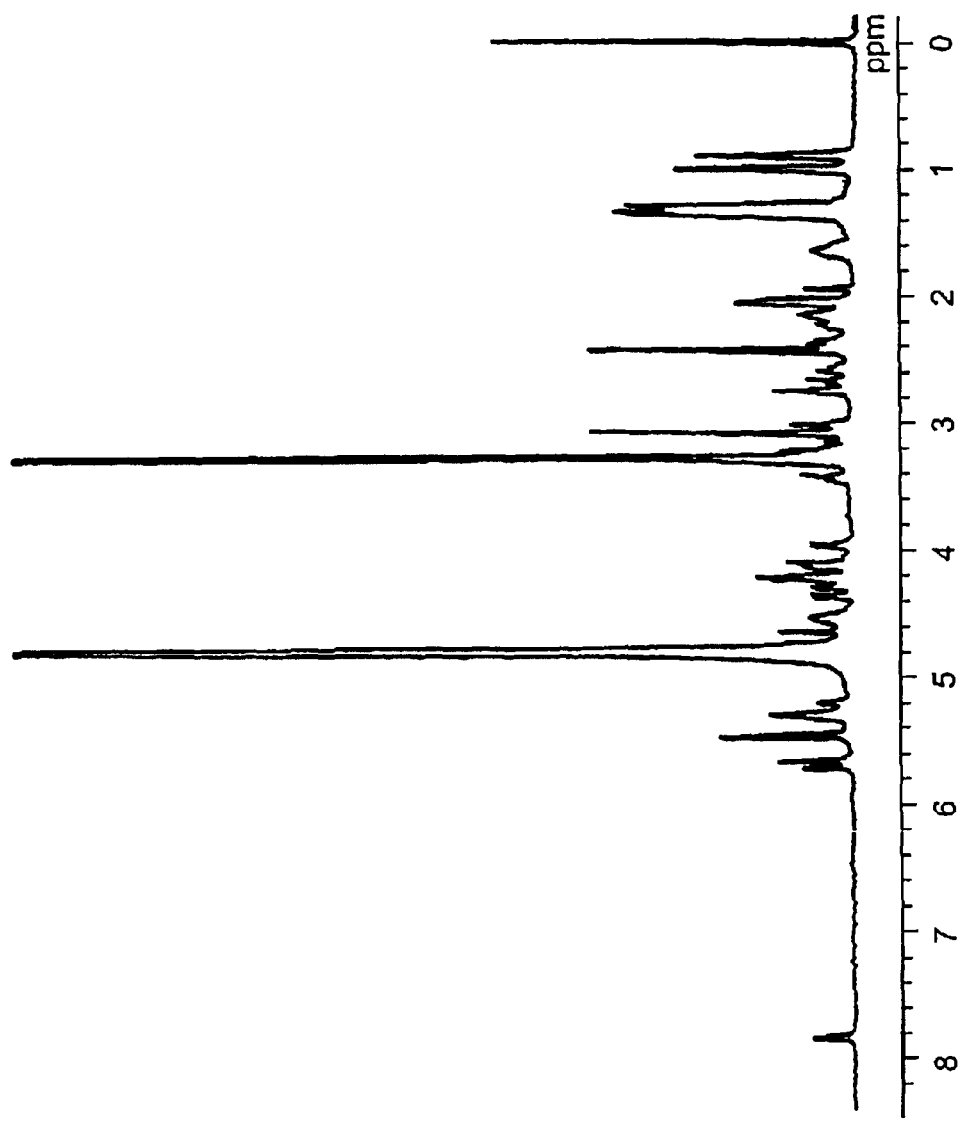
FIG. 5 demonstrates $^1$H-NMR spectrum (500 MHz, CD$_3$OD) of liposidomycins K.
Figure 6:
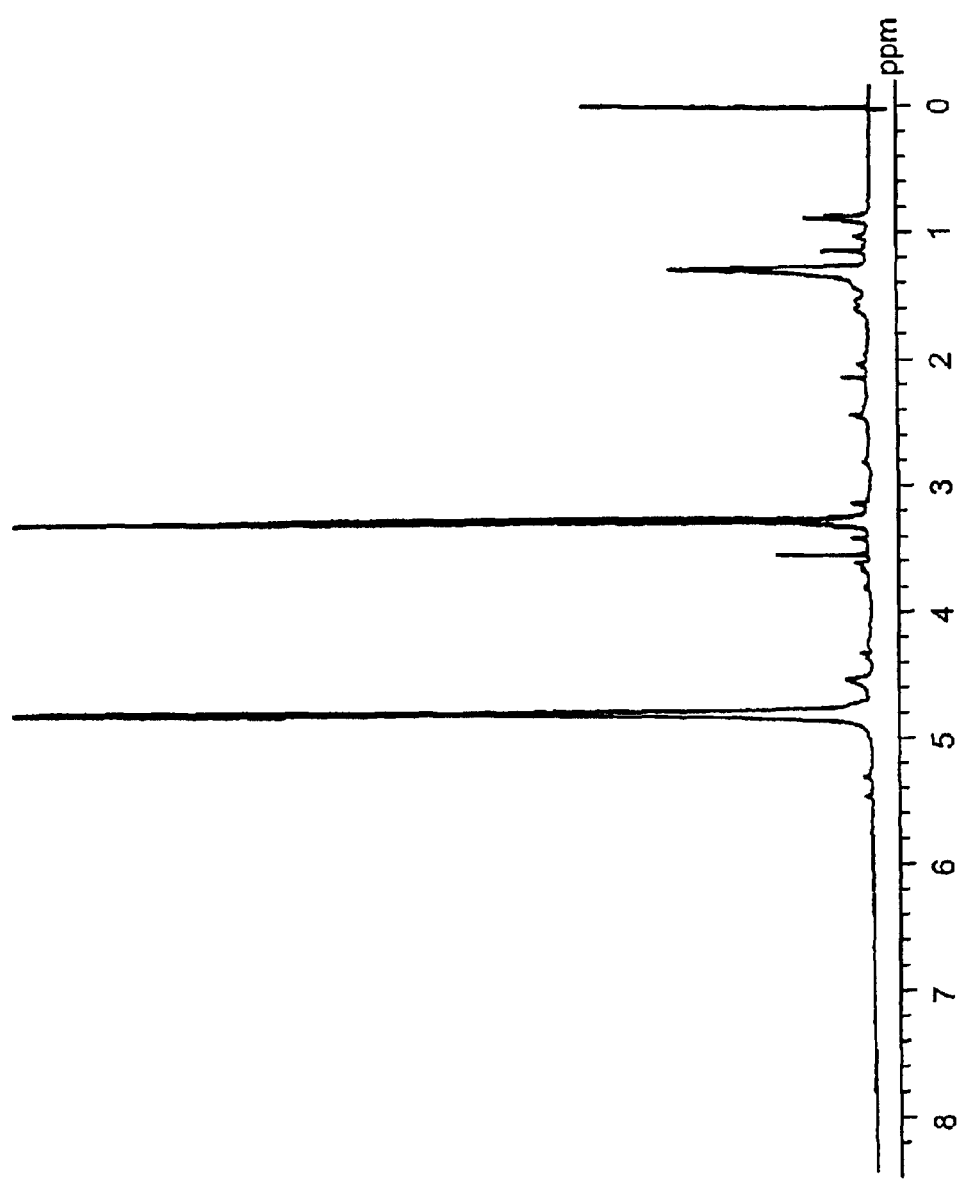
FIG. 6 demonstrates $^1$H-NMR spectrum (500 MHz, CD$_3$OD) of liposidomycins N.
Figure 7:
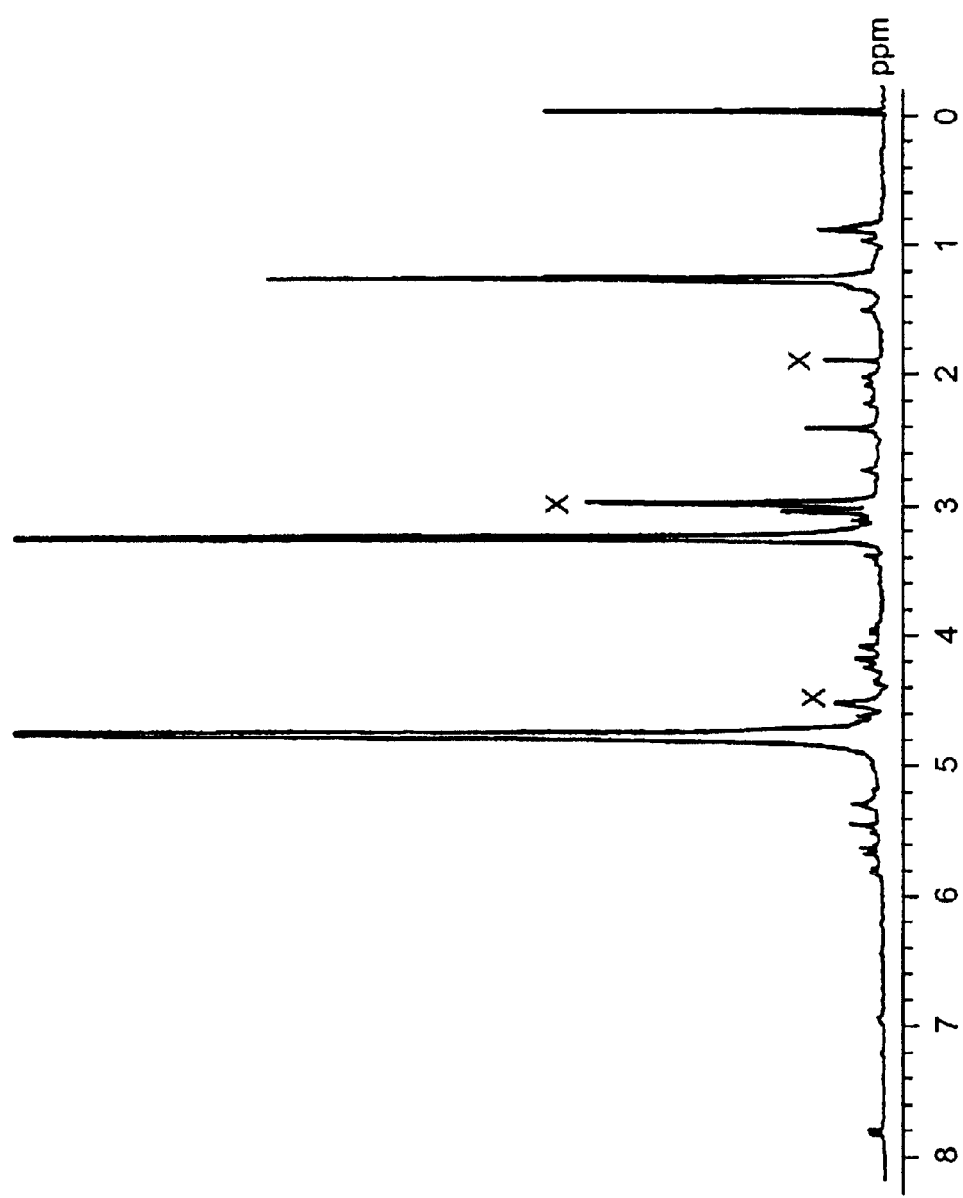
FIG. 7 demonstrates $^1$H-NMR spectrum (500 MHz, CD$_3$OD) of liposidomycins A-(II) and x represents peaks unrelated to the substance of the present invention.
Figure 8:
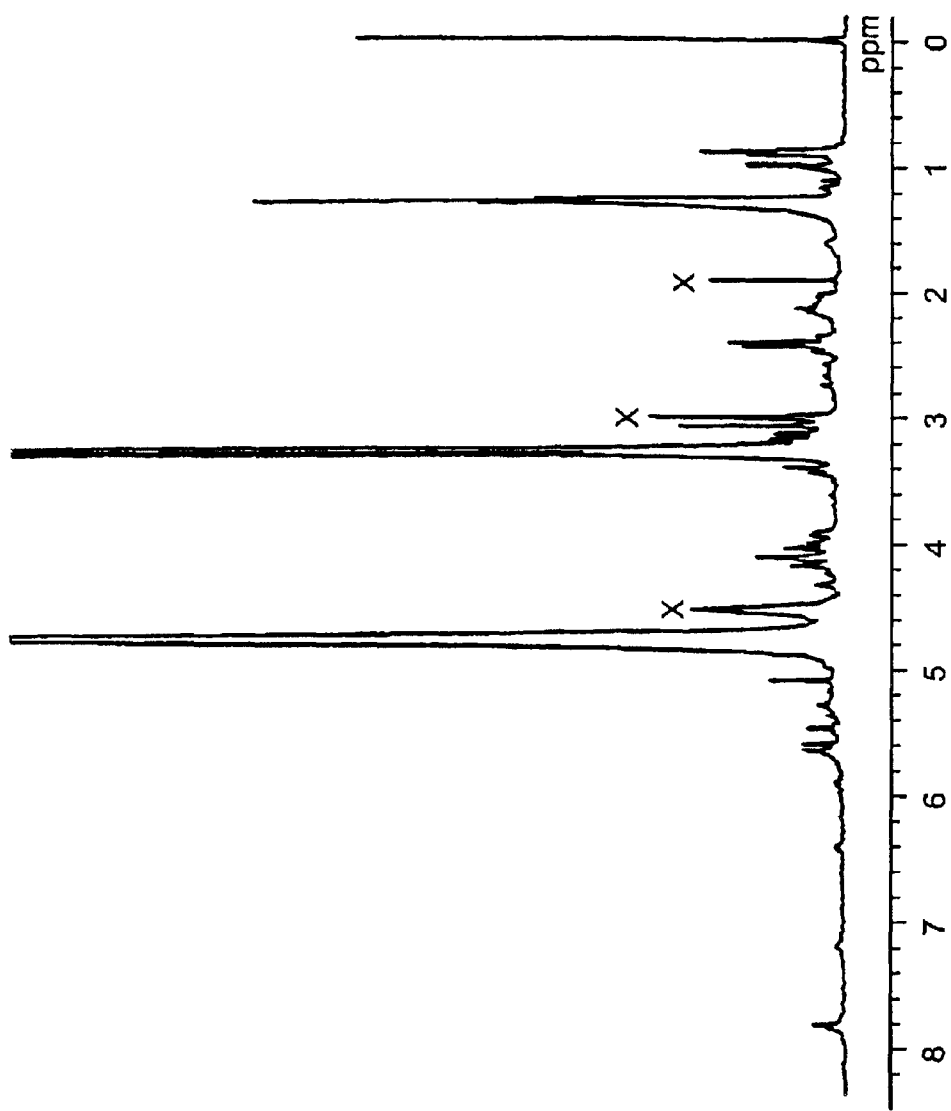
FIG. 8 demonstrates $^1$H-NMR spectrum (500 MHz, CD$_3$OD) of liposidomycins X-(III) and x represents peaks unrelated to the substance of the present invention.
Figure 9:
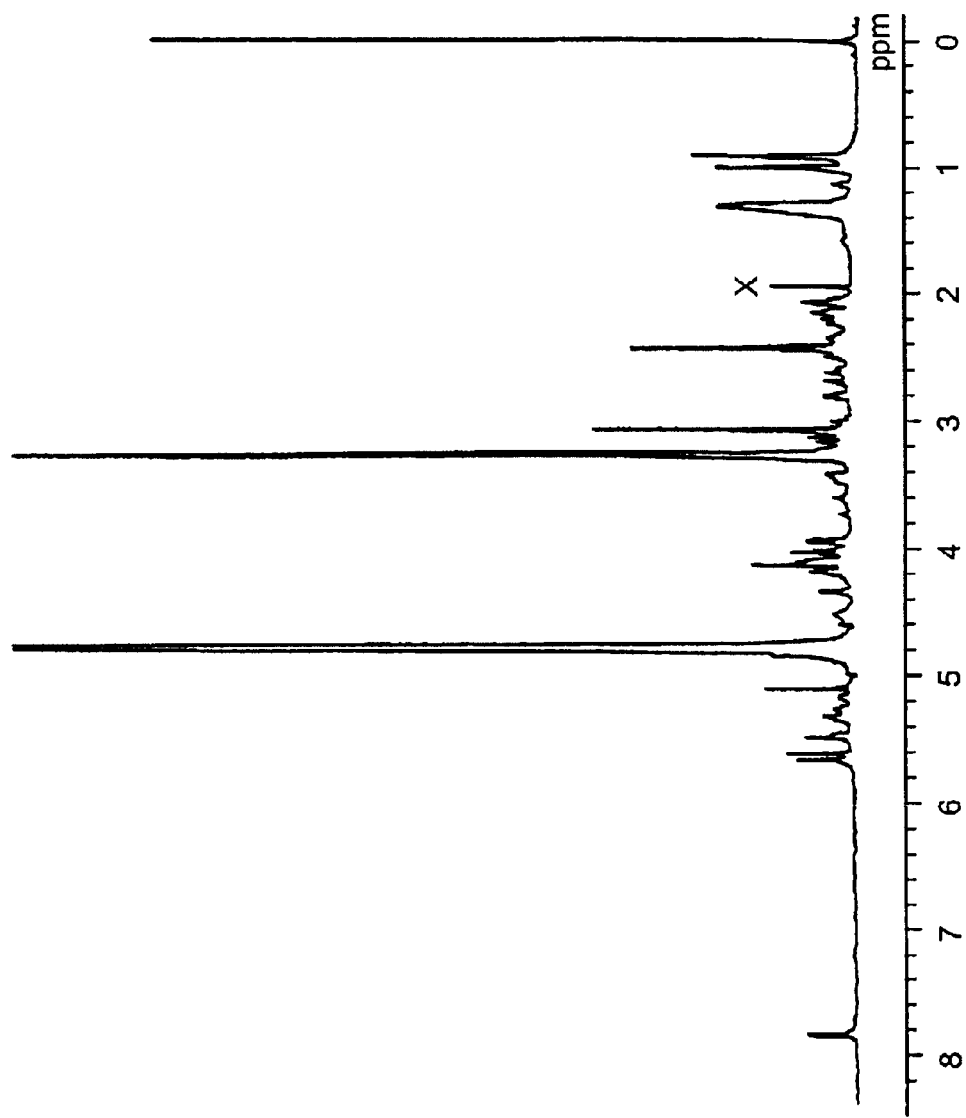
FIG. 9 demonstrates $^1$H-NMR spectrum (500 MHz, CD$_3$OD) of liposidomycins Y-(III) and x represents peaks unrelated to the substance of the present invention.
Figure 10:
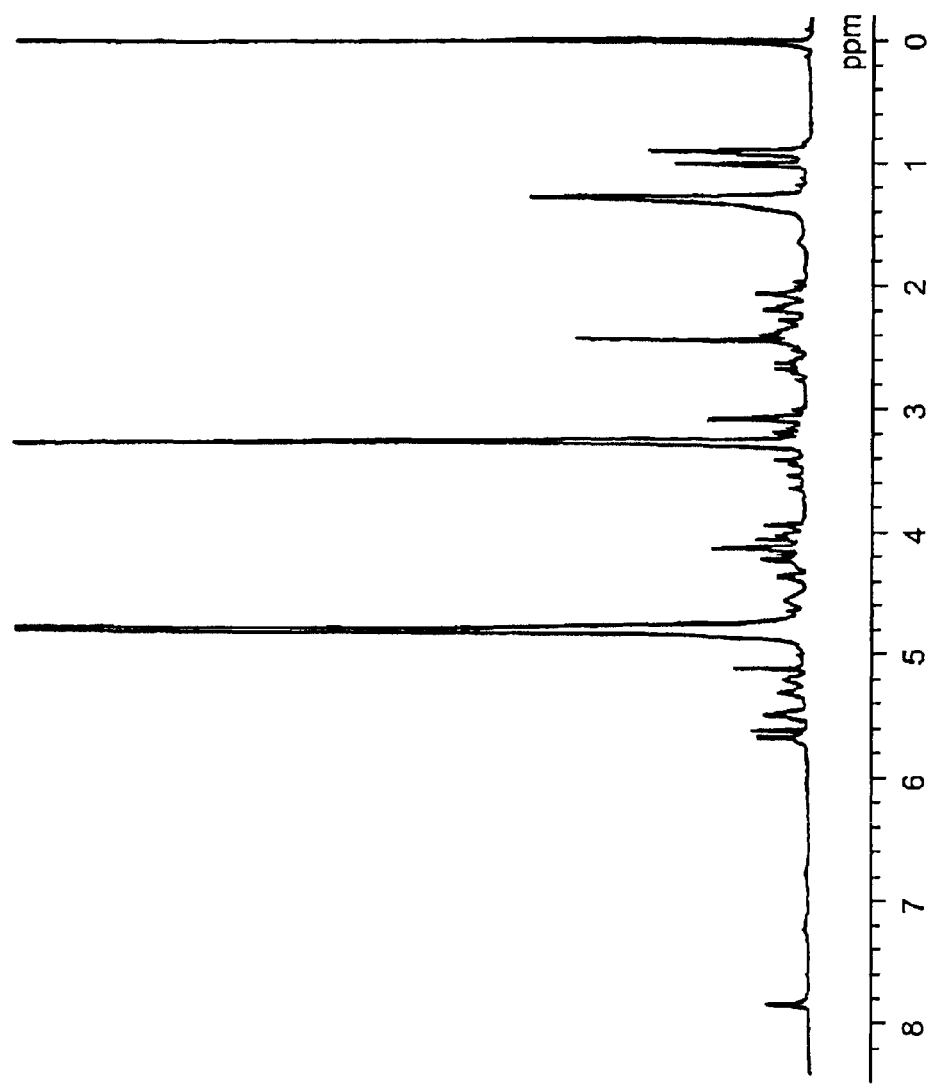
FIG. 10 demonstrates $^1$H-NMR spectrum (500 MHz, CD$_3$OD) of liposidomycins Z-(III) and x represents peaks unrelated to the substance of the present invention.
Figure 12:
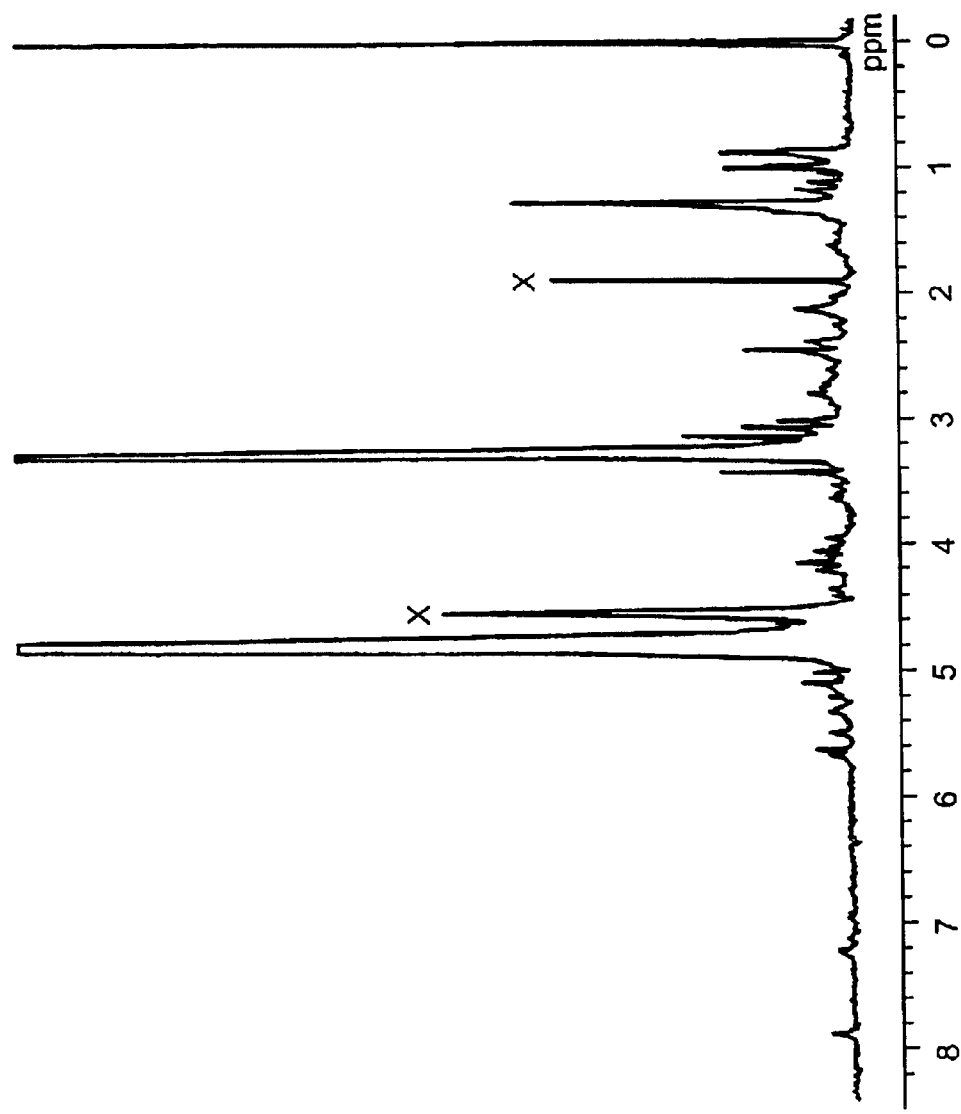
FIG. 12 demonstrates $^1$H-NMR spectrum (500 MHz, CD$_3$OD) of liposidomycins V-(III) and x represents peaks unrelated to the substance of the present invention.
Figure 13:
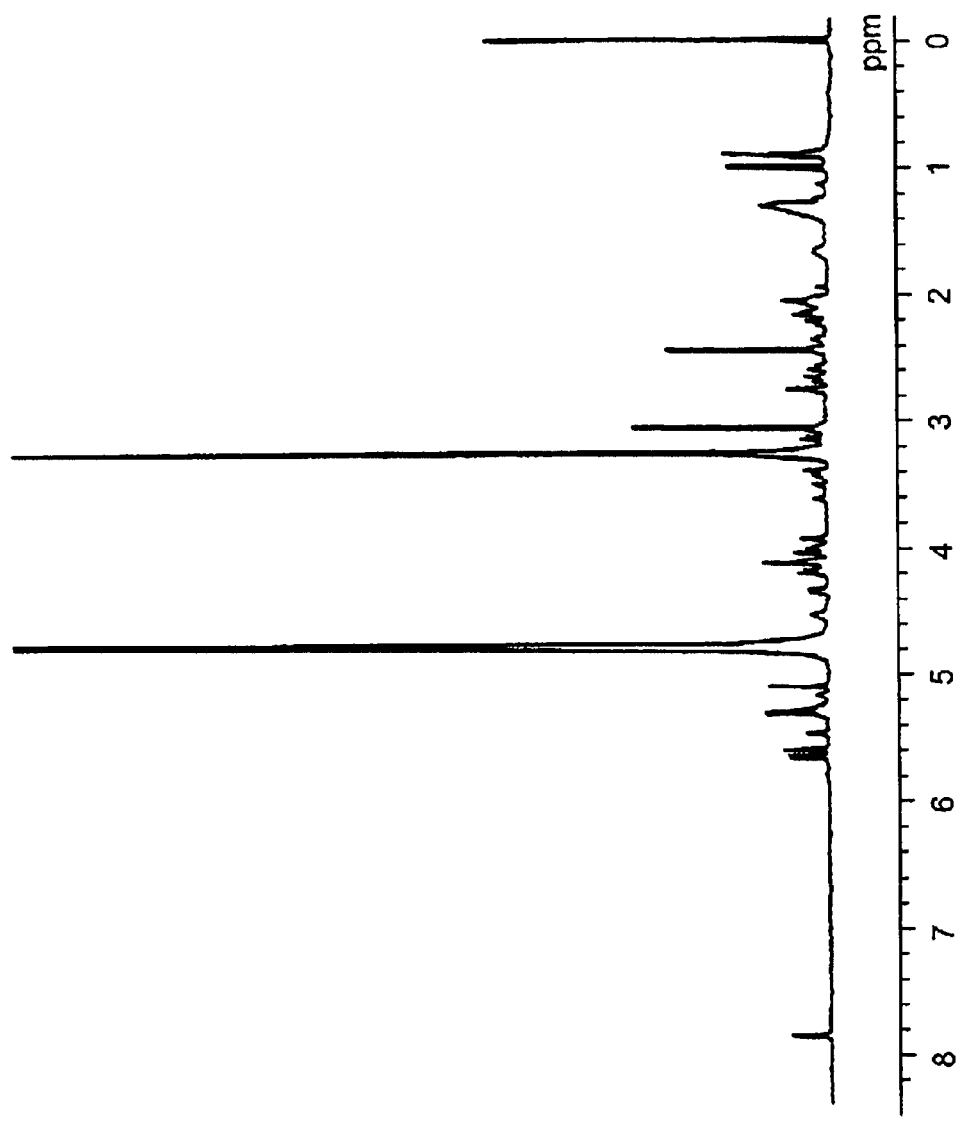
FIG. 13 demonstrates $^1$H-NMR spectrum (500 MHz, CD$_3$OD) of liposidomycins A-(III) and x represents peaks unrelated to the substance of the present invention.
Figure 14:
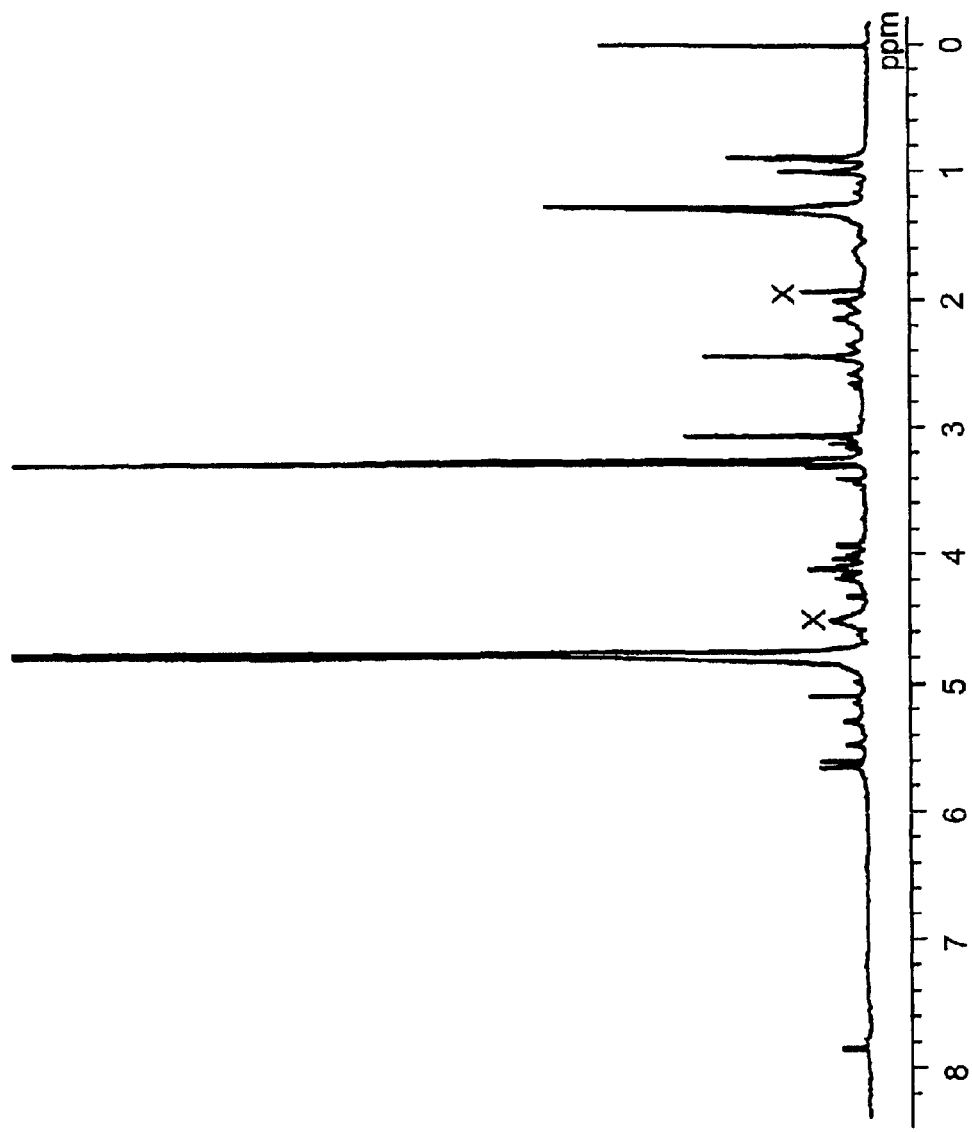
FIG. 14 demonstrates $^1$H-NMR spectrum (500 MHz, CD$_3$OD) of liposidomycins G-(III) and x represents peaks unrelated to the substance of the present invention.
Figure 15:
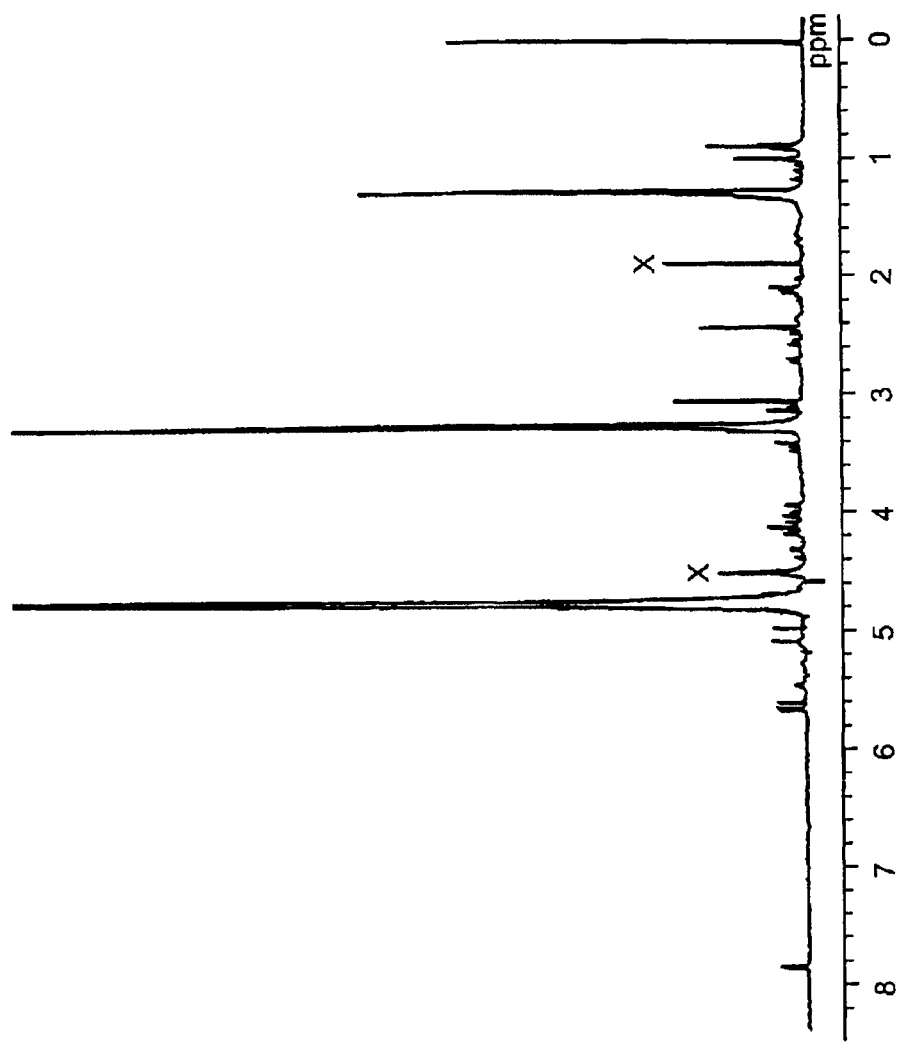
FIG. 15 demonstrates $^1$H-NMR spectrum (500 MHz, CD$_3$OD) of liposidomycins M-(III) and x represents peaks unrelated to the substance of the present invention.
Figure 16:
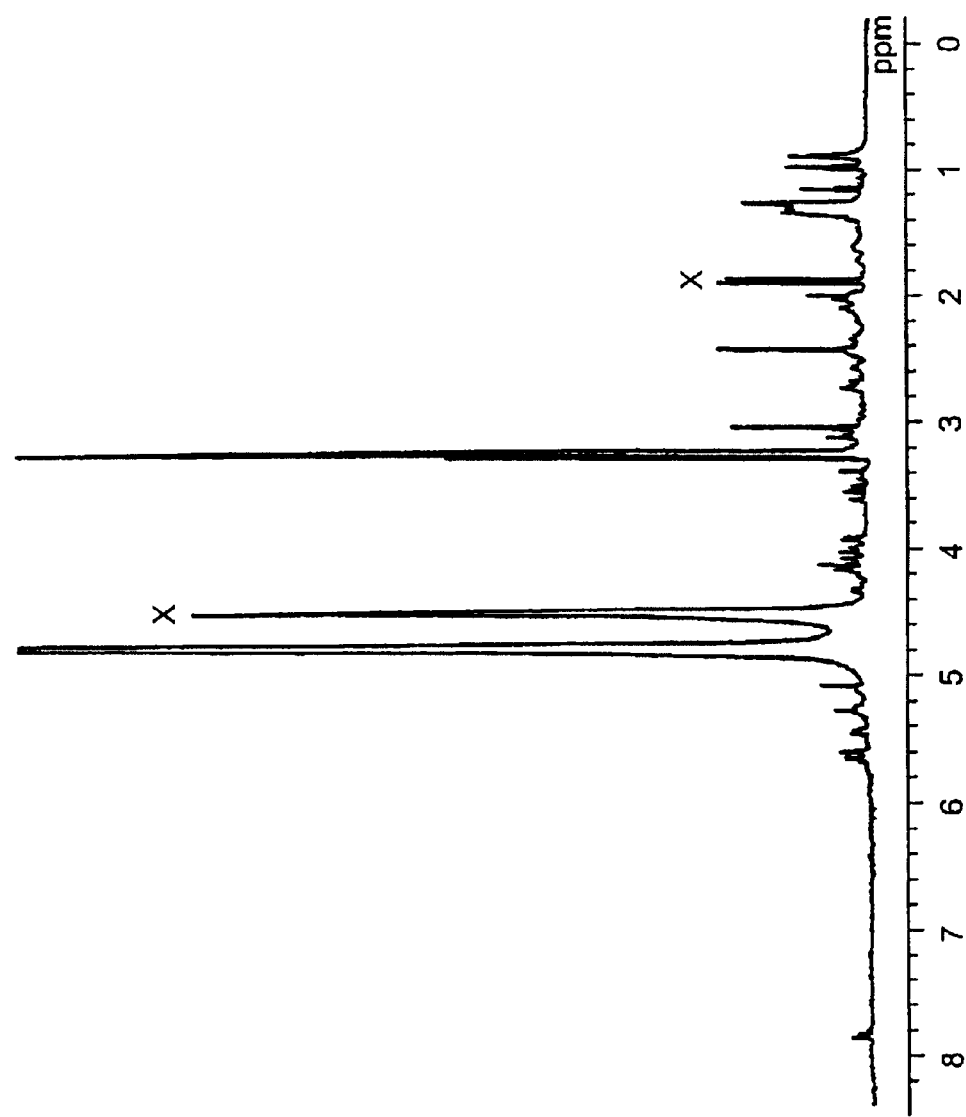
FIG. 16 demonstrates $^1$H-NMR spectrum (500 MHz, CD$_3$OD) of liposidomycins K-(III) and x represents peaks unrelated to the substance of the present invention.
Figure 17:
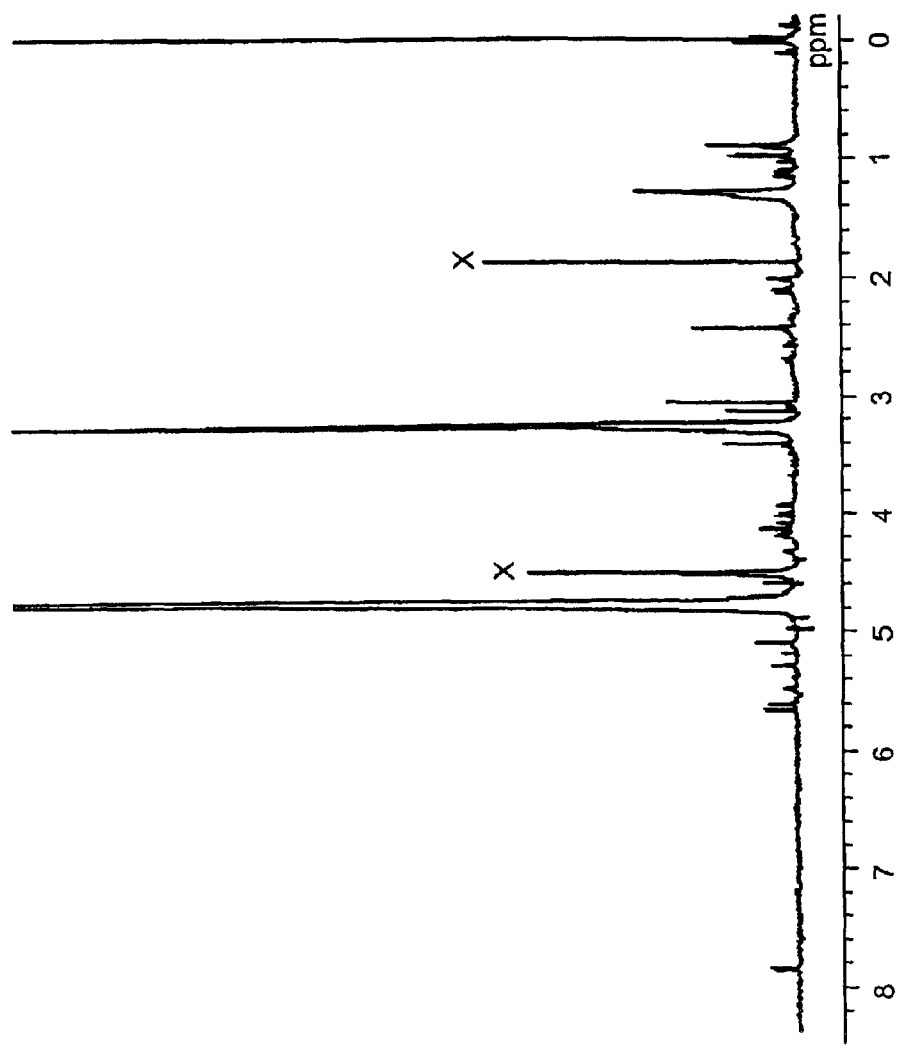
FIG. 17 demonstrates $^1$H-NMR spectrum (500 MHz, CD$_3$OD) of liposidomycins N-(III) and x represents peaks unrelated to the substance of the present invention.
Figure 18:
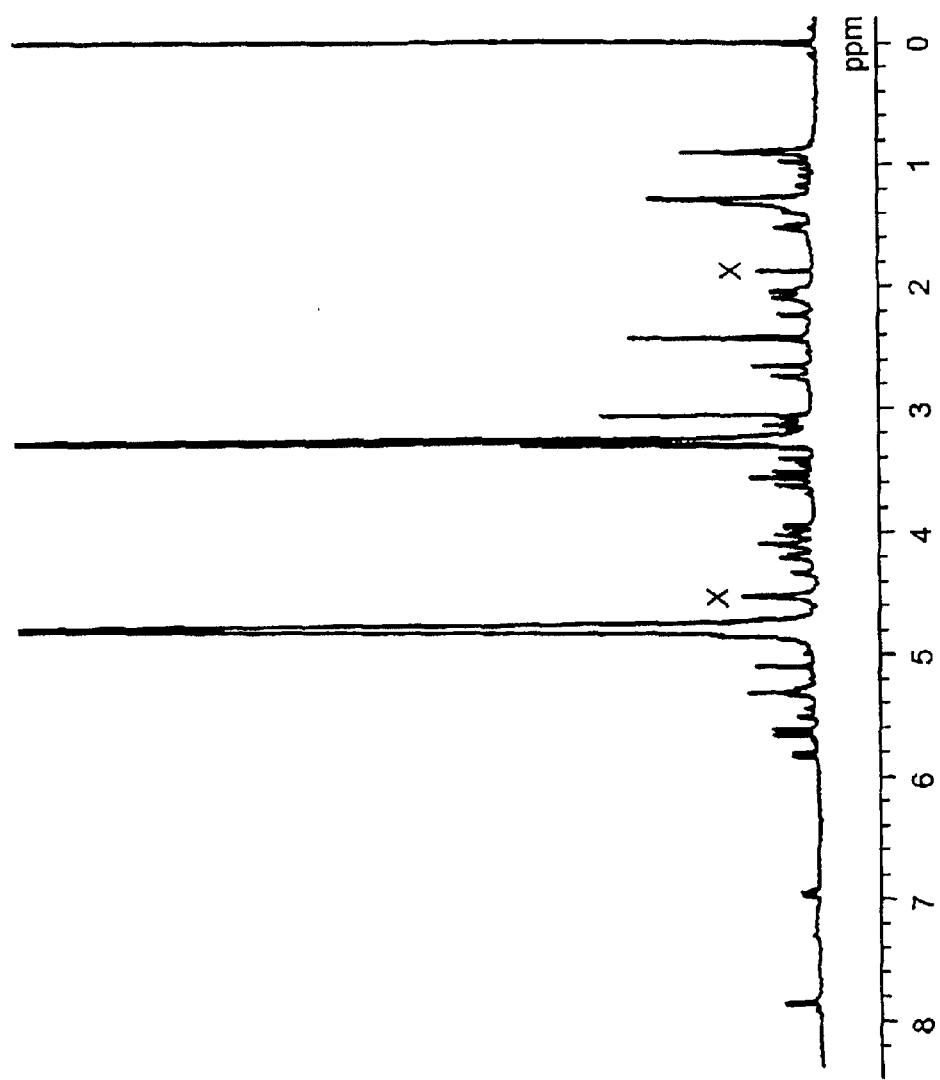
FIG. 18 demonstrates $^1$H-NMR spectrum (500 MHz, CD$_3$OD) of liposidomycins A-(IV) and x represents peaks unrelated to the substance of the present invention.

(5) Ultraviolet absorption spectrum: Each component has maximum absorption at 261–263 nm (50% methanol).
(6) Infrared absorption spectrum (KBr tablet): Infrared absorption spectrum of liposidomycins Z-(III) is shown in FIG. 1.
(7) $^1$H-NMR spectrum: 500 MHz, in deuterated methanol, room temperature. The spectrum of each compound is shown respectively as follows: liposidomycins Z (FIG. 2), L (FIG. 3), M (FIG. 4), K (FIG. 5), N (FIG. 6), A-(II) (FIG. 7), X-(III) (FIG. 8), Y-(III) (FIG. 9), Z-(III) (FIG. 10), C-(III) (FIG. 11), V-(III) (FIG. 12), A-(III) (FIG. 13), G-(III) (FIG. 14), M-(III) (FIG. 15), K-(III) (FIG. 16), N-(III) (FIG. 17), A-(IV) (FIG. 18).

Figure 11:
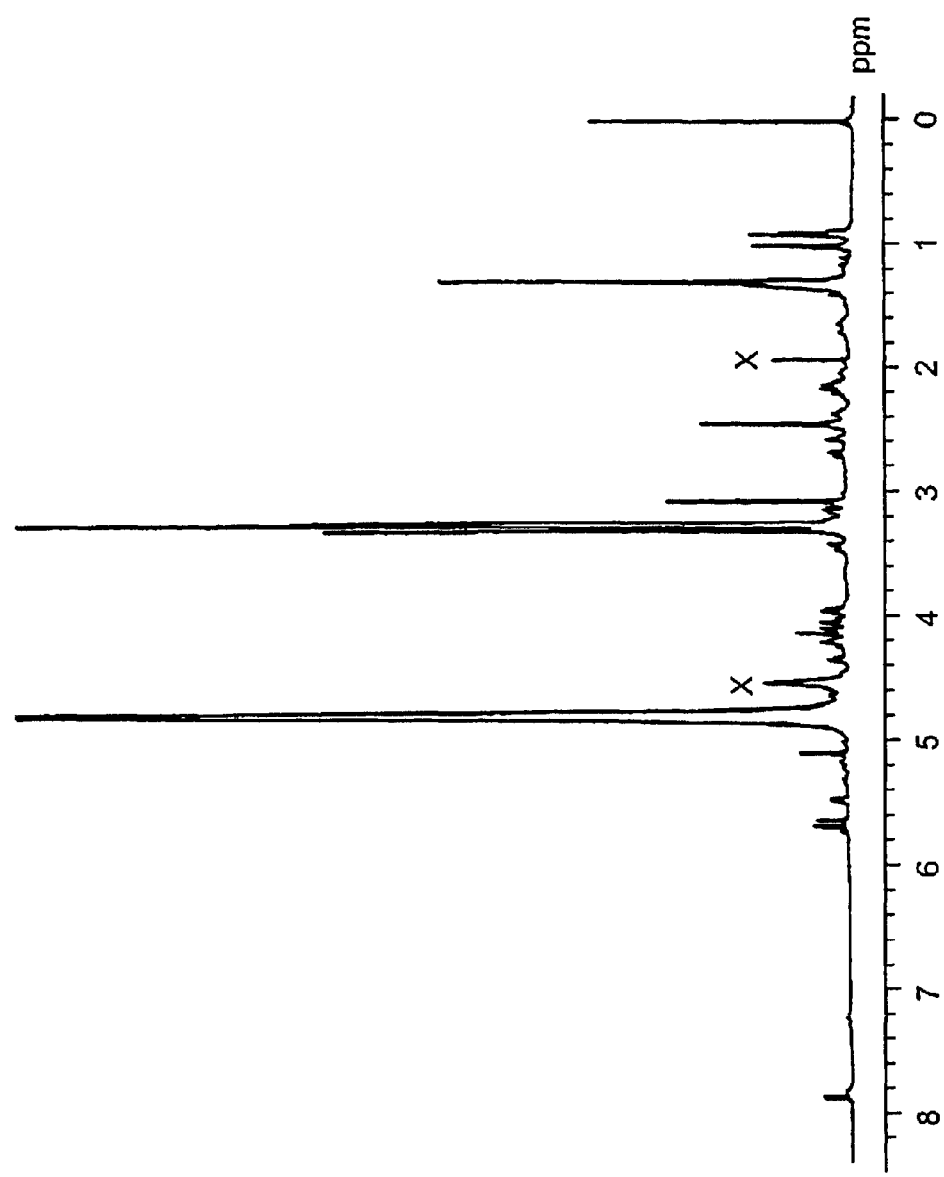
FIG. 11 demonstrates $^1$H-NMR spectrum (500 MHz, CD$_3$OD) of liposidomycins C-(III) and x represents peaks unrelated to the substance of the present invention.

Though the molecular formula, $C_{42}H_{67}N_5O_{16}$ of liposidomycins C-(III) which has not sulfate group is the same as that of liposidomycins B which has not sulfate group (CAS registered number thereof: 113378-45-3), the former compound has one methyl group at the end of aliphatic side-chain according to $^1$H-NMR spectrum of FIG. 11 (t, 0.89 ppm, 3H), which can be distinguished from liposidomycins B without sulfate group (2 methyl groups at the end of side-chain thereof, iso-type).

(8) Solubility: Each component is soluble in methanol, dimethyl sulfoxide, water but insoluble in hexane and chloroform.
(9) Rf value in TLC: Rf value in the case of TLC (silica gel Art. 5715 (Merk)) developed by butanol/acetic acid/water (4:1:2).

compounds with sulfate group (type (I), (II)): 0.35
compounds without sulfate group (type (III), (IV)): 0.41

(10) Retention time in HPLC: Retention time of each component under 2 different conditions is shown in Table 2.

TABLE 2

| | Retention time (minutes) | |
|---|---|---|
| | Conditions 1 | conditions 2 |
| (I) Type I(having both sulfate group and 3-methylglutaric acid residue) | | |
| 1. Z: | 14.5 | |
| 2. L: | | 8.2 |
| 3. M: | | 8.8 |
| 4. K: | 51.8 | 7.0 |
| 5. N: | | 11.0 |
| (II) Type II (having sulfate group but not 3-methylglutaric acid residue) | | |
| 1. A-(II): | 16.6 | |
| (III) Type III (having 3-methylglutaric acid residue but not sulfate group) | | |
| 2. X-(III): | 13.9 | |
| 3. Y-(III): | 9.1 | |
| 4. Z-(III): | 15.8 | |
| 5. C-(III): | 25.9 | |
| 6. V-(III): | 12.6 | |
| 7. A-(III): | 21.5 | |
| 8. G-(III): | 41.9 | 6.6 |
| 9. M-(III): | | 11.0 |
| 10. K-(III): | | 8.3 |
| 11. N-(III): | | 14.0 |
| (IV) Type IV (having neither sulfate group or 3-methylglutaric acid residue) | | |
| 1. A-(IV): | | 18.8 | conditions 1: 40% CH$_3$CN-0.1% DEA-HCOOH(pH4), 254 nm, 1.5 ml/min, PEGASIL ODS (4.6φ × 250 mm, Sensyu-kagaku)
conditions 2: 50% CH$_3$CN-0.1% DEA-HCOOH(pH4), 254 nm, 1.5 ml/min, PEGASIL ODS (4.6φ × 250 mm, Sensyu-kagaku)

(11) Strucuture of aliphatic side-chain R$_1$

Type (I)
  Z: double bond in position 5–6
  L: iso-type
  M: normal type
  K: double bonds in position 9–10 and 12–13
  N: double bond in position 9–10

Type (III)
  Y-(III): double bonds in position 5–6 and 8–9
  Z-(III): double bond in position 5–6
  A-(III): double bonds in position 7–8 and 10–11
  G-(III): double bond in position 7–8
  M-(III): normal type
  K-(III): double bonds in position 9–10 and 12–13
  N-(III): double bond in position 9–10

EXAMPLE

The present invention will be described below by exemplifying examples but the scope of the invention will not be limited by these examples.

Example 1
Production of RK-1061 whose R$_3$ Group is Sulfate Group or Hydrogen (RK-1061 with Sulfate Group and RK-1061 without Sulfate Group)

The aforementioned RK-1061 cell line cultured in agar slant culture medium was inoculated in a 500 ml Erlenmeyer flask containing 70 ml of liquid medium (pH6.8) comprising 2% glucose, 1% soluble starch, 0.1% meat extract, 0.4% yeast extract, 2.5% soy bean powder, 0.2% sodium chloride and 0.005% potassium secondary phosphate and cultured at 28° C. for 2 days. One ml of the culture medium was inoculated in another flask containing the same culture medium as the above and cultured for 48–72 hours. Further, 140 ml of this culture medium was inoculated into a 30 liters jar fermenter containing 18 liters of the same medium as the above and cultured by aeration and stirring under the following conditions at 28° C. for 65–90 hours until pH thereof became over 8.4:

aeration rate: 18 liters/minute and
  stirring rate: 350 rpm.

After the fermentation, culture supernatant (pH 8.8, the diameter of growth inhibition against Mycobacterium phlei was 20.2 mm) was separated from mycelium (2.9 kg, the diameter of growth inhibition against Mycobacterium phlei was 24.3 mm) and the mycelium was extracted with 5 liters of acetone overnight. Aqueous solution obtained by evaporating acetone from the extract solution under vacuum was combined with the culture supernatant and the same volume of butanol was added thereto followed by 3 times extraction. The butanol layer was condensed under vacuum to yield about 60 g of crude extract, which was dissolved in 80 ml of methanol. Then, 240 ml of chloroform was added thereto, which was applied on a silica gel column(8×12 cm, Merk, 70–230 mesh) saturated with chloroform/methanol (3:1) and contaminants were excluded with chloroform/methanol (2:1) and chloroform/methanol (1:1). Then, active substance was eluted with chloroform/methanol (1:2) and chloroform/methanol (1:3).

The eluate was condensed under vacuum to yield about 14 g of crude extract, which was dissolved in 20 ml methanol and applied and fractionated on a LH-20 column (3×79 cm, Pharmacia) to yield 10.3 g of an active substance. Further, this was applied on a silica gel column (8×12 cm) saturated with butanol/methanol/water (4:1:2) and eluted with the same solvent as the above to yield an active substance (6.5 g).

Then, this was fractionated by HPLC. Firstly, this was separated into 6 fractions using Senshu-pak ODS (20φ×250 mm, ODS-5251-SS, Senshu-kagaku) and acetonitrile-0.1% diethylamine/formic acid (pH 4) (40:60) as eluent at flowing rate of 10 ml/min, and further these fractions were fractionated into 6 fractions using the same column the same flow rate and acetonitrile-0.1% diethylamine/formic acid (pH 4.0) (60:40). These fractions were condensed under vacuum and refractionated using Capcell pak ODS (20φ×250 mm, SG-120, Shiseido) under the same conditions as the above respectively. Each liposidomycin fractions obtained as the above was condensed under vacuum to remove acetonitrile. Water was added to each fraction for desalting, which was applied on MCI GEL (1×5 cm, Mitsubishi kasei), washed with sufficient water, eluted with 50% acetone, condensed under vacuum and freeze-dried to yield white powder of liposidomycins as active substance.

Example 2
Production of RK-1061 whose R$_3$ Group is Sulfate Group or Hydrogen (RK-1061 with Sulfate Group and RK-1061 without Sulfate Group)

The aforementioned SN-1061M cell line cultured in agar slant culture medium was inoculated in a 500 ml Erlenmeyer flask containing 70 ml of liquid medium (pH6.7) (C4 medium) comprising 2% glucose, 1% soluble starch, 0.1% meat extract, 0.4% yeast extract, 2.5% soy bean powder, 0.2% sodium chloride and 0.005% potassium secondary phosphate and cultured at 27° C. for 2 days. One ml of this medium was inoculated into a flask containing the same medium as the above and cultured for 5 days. The culture medium was separated into culture supernatant and mycelium by centrifugation and mycelium was weighed and pH of the supernatant was measured. an antibacterial activity of extracted material from mycelium with acetone was studied. An antibacterial activity was assayed by measuring the diameter of the inhibition zone on a paper disk (the diameter thereof was 8 mm) sunk by 40 μl of the culture medium after culture against *Mycobacterium phlei* and *Escherichia coli* BE under suitable conditions.

Figure 19:
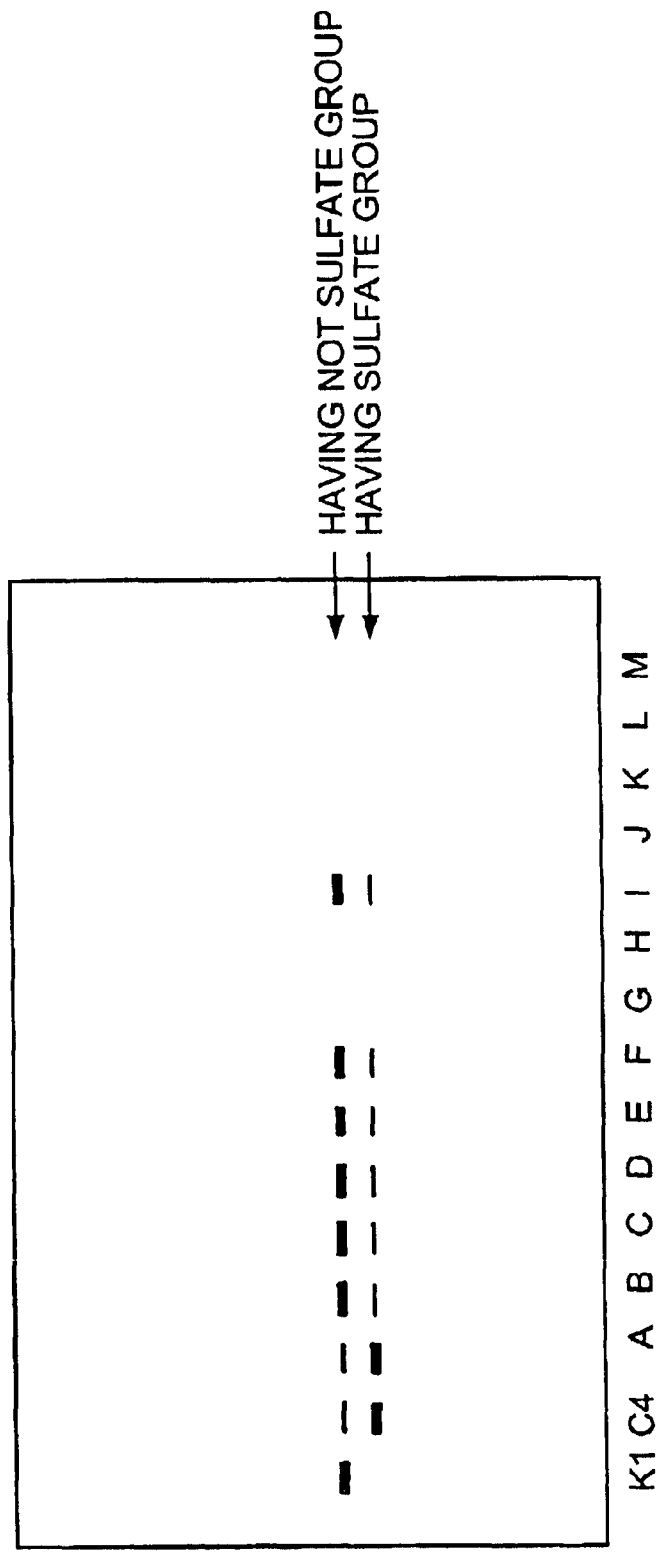
FIG. 19 demonstrates TLC of liposidomycins (RK-1061s) obtained in example 2, example 3 and example 4. As carbon source of culture media, A: maltose, B: xylose, C: lactose, D: D-fructose, E: sucrose, F: inositol, G: L-rhamnose, H: L-arabinose, I: D-mannitol, J: raffinose, K: salicin, L: L-sorbose, M: D-glucosamine.
Figure 20:
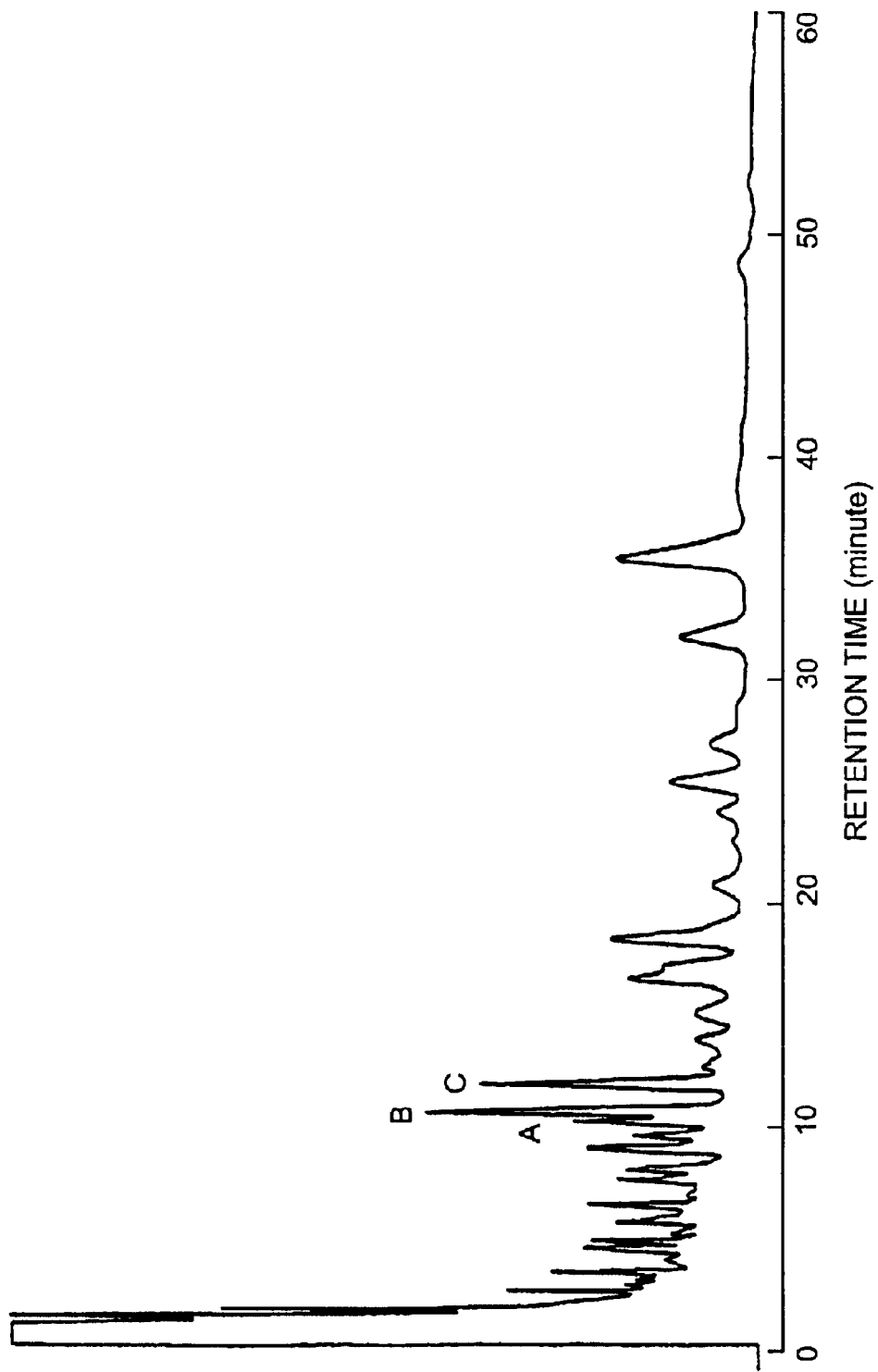
FIG. 20 demonstrates HPLC of liposidomycins (RK-1061s) obtained in example 2.

Further, the culture supernatant and mycelium extract were extracted with butanol and condensed to dried up respectively, which were dissolved in 1/10 vol. of methanol to be analyzed by HPLC and TLC. HPLC analysis was carried out using acetonitrile/0.1% diethylamine-formic acid (pH 4.0) (45:55) as an eluent (flowing rate: 1.5 ml/min. and detected at 254 nm) and a Capell pak ODS column (4.6φ× 250 mm, Shiseido). TLC was carried out using silica gel Art. 5715 (0.25 mm, Merk) and butanol-acetic acid-water (4:1:2) as a developing solvent. The results of antibacterial effects are shown in Table 3 and the results of TLC and HPLC are shown in FIG. 19 and FIG. 20 respectively. Culture replacing glucose in culture medium into maltose was also carried out as the above.

Example 3

Production of RK-1061 whose $R_3$ is Hydrogen Atom (RK-1061 without Sulfate Group)

The SN-1061M cell line cultured in agar slant medium was inoculated into a 500 ml Erlenmeyer flask containing 70 ml of liquid medium replacing glucose as carbon source in the medium (C4 medium) described in example 2 into one selected from the group consisting of xylose, lactose, D-fructose, sucrose, inositol or D-mannitol, which was cultured at 27° C. by stirring at 200 rpm for 2–4 days. Two ml of the culture medium was inoculated into a Erlenmeyer flask containing the same medium as the above and cultured under the same conditions as the above for 5 days and it was found that an active component without sulfate group was specifically produced. The culture medium was centrifuged to separate culture supernatant and mycelium. The mycelium was weighed and pH of the supernatant was measured. Antibacterial activity of acetone extract of mycelium was studied. An antibacterial activity was assayed by measuring the diameter of cell growth inhibition zone on a paper disk (the diameter thereof was 8 mm) sunk by 40 μl of the culture medium after culture against *Mycobacterium phlei* and *Escherichia coli* BE under suitable conditions.

Further, the culture supernatant and the mycelium extract were extracted with butanol, condensed and dried up, which were dissolved in 1/10 vol. of methanol and HPLC and TLC analysis thereof were carried out. HPLC analysis was carried out using acetonitrile-0.1% diethylamine/formic acid (pH 4.0) (45:55) as an eluent (flowing rate: 1.5 ml/min. and detected at 254 nm) and a Capcell pak ODS column (4.6φ× 250 mm, Shiseido). TLC was carried out using silica gel Art. 5715 (0.25 mm, Merk) and butanol-acetic acid-water(4:1:2) as a developing solvent. The results of antibacterial effects are shown in Table 3 and the results of TLC are shown in FIG. 19.

Example 4

Production of RK-1061 whose $R_3$ is Hydrogen Atom (RK-1061 without Sulfate Group)

The SN-1061M cell line cultured in agar slant medium was inoculated into a 500 ml Erlenmeyer flask containing 70 ml of medium (K1 medium) comprising 40 g of sucrose (Wako-junyaku), 30 g of soy bean powder (Honen-seiyu), 20 g of wheat germ (Sigma) or malt extract (Difco), 6 g of sodium chloride (Wako-junyaku) and adjusted at pH 7.0, which was cultured at 27° C. by stirring at 200 rpm for 2–4 days. Two ml of the culture medium was inoculated into a Erlenmeyer flask containing the same medium as the above and cultured under the same conditions as the above for 5 days and it was found that an active component without sulfate group was specifically produced. The culture medium was centrifuged to separate culture supernatant and mycelium. The mycelium was weighed and pH of the supernatant was measured. Antibacterial activity of acetone extract of mycelium was studied. An antibacterial activity was assayed by measuring the diameter of the cell growth inhibition zone on a paper disk (the diameter thereof was 8 mm) sunk by 40 μl of the culture medium after culture against *Mycobacterium phlei* and *Escherichia coli* BE under suitable conditions.

Figure 21:
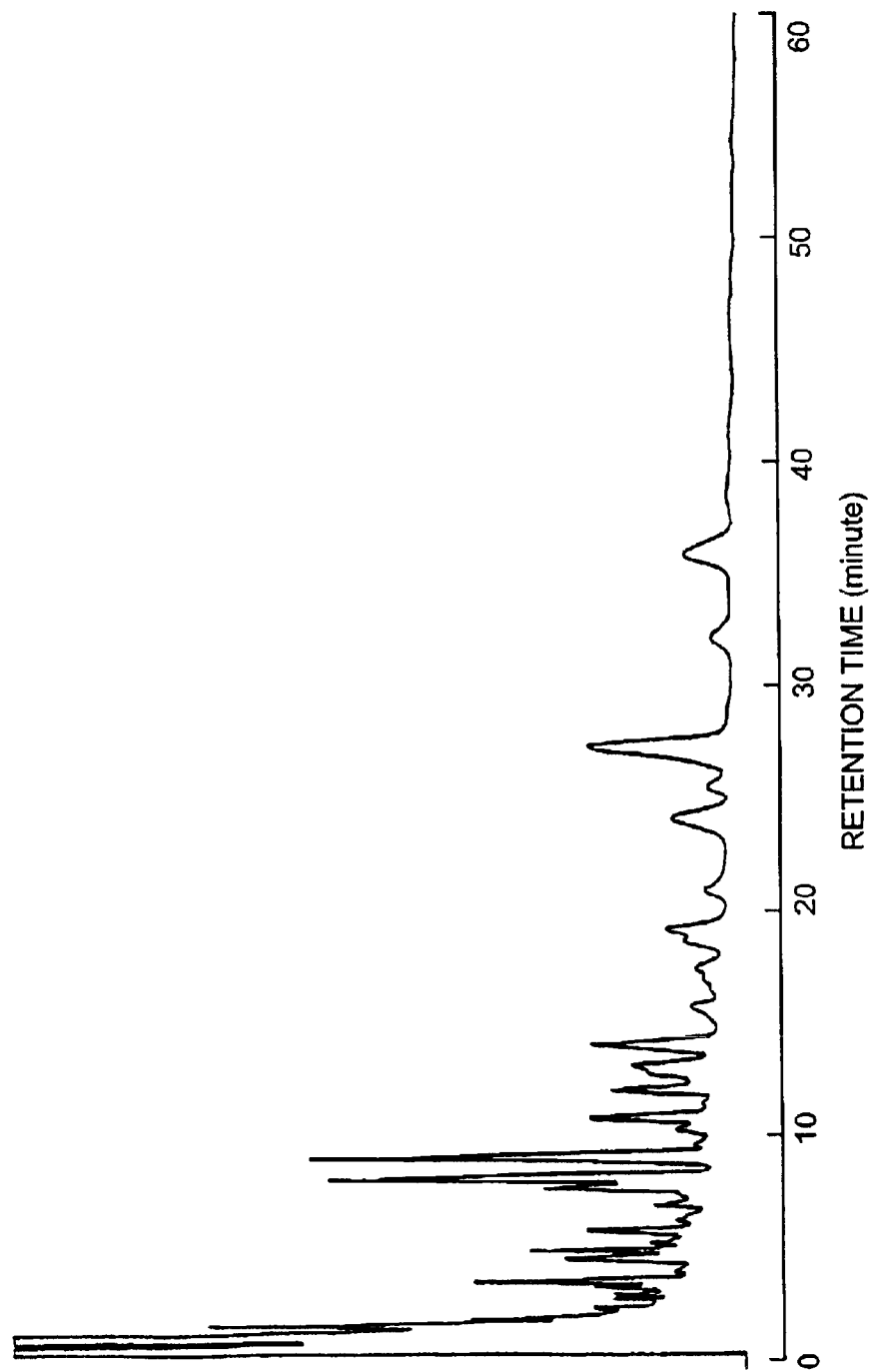
FIG. 21 demonstrates HPLC of liposidomycins (RK-1061s) obtained in example 4.

Further, the culture supernatant and the mycelium extract were extracted further with butanol, condensed and dried up, which were dissolved in 1/10 vol. of methanol and HPLC and TLC analysis thereof were carried out. HPLC analysis was carried out using acetonitrile-0.1% diethylamine/formic acid (pH 4.0) (45:55) as an eluent (flowing rate:1.5 ml/min. and detected at 254 nm) and a Capcell pak ODS column (4.6φ× 250 mm, Shiseido). TLC was carried out using silica gel Art. 5715 (0.25 mm, Merk) and butanol-acetic acid-water (4:1:2) as a developing solvent. The results of antibacterial effects are shown in Table 3 and the results of TLC and HPLC are shown in FIG. 19 and FIG. 21 respectively.

TABLE 3

| Carbon source | The volume of mycelium (wet vol. %) | pH | The diameter of cell growth inhibition zone | | | |
|---|---|---|---|---|---|---|
| | | | B(BE)M | | B(Ph)M | |
| (C4 medium) | 42 | | + | + | 16.6 | 19.7 |
| (K1 medium) | 51 | | 9.8 | 11.6 | 11.9 | 20.4 |
| A Maltose | 41 | 7.9 | + | 0 | 13.9 | 17.7 |
| B Xylose | 44 | 6.5 | 10.2 | (12.1) | 16.0 | 20.8 |
| C Lactose | 45 | 7.5 | 11.9 | 11.4 | 18.9 | 22.0 |
| D D-Fructose | 46 | 7.8 | 12.2 | 11.5 | 20.6 | 23.3 |
| E Sucrose | 49 | 7.9 | 13.6 | 12.7 | 23.4 | 23.8 |
| F Inositol | 35 | 7.9 | 13.1 | 10.7 | 20.2 | 20.0 |
| G L-Rhamnose | 25 | 8.4 | 0 | 0 | 0 | 0 |
| H L-Arabinose | 26 | 4.8 | 0 | 0 | 0 | 0 |
| I D-Mannitol | 39 | 7.8 | 13.2 | 11.5 | 20.2 | 21.1 |
| J Raffinose | 18 | 8.6 | 0 | 0 | 0 | 0 |
| K Salicin | 13 | 8.6 | 0 | 0 | 0 | 0 |
| L L-Sorbose | 20 | 8.6 | 0 | 0 | 0 | 0 |
| M D-Glucosamine | 6 | 3.7 | 0 | 0 | 0 | 0 |

BE: *Escherichia coli* BE 1186
B: culture supernatant
Ph: *Mycobacterium phlei* IFO 3158
M: mycelium extract

Example 5

Production of RK-1061 whose $R_3$ Group is Hydrogen Atom (RK-1061 without Sulfate Group)

The aforementioned SN-1061M cell line (FERM BP-5800) cultured in agar slant culture medium was inoculated in a 500 ml Erlenmeyer flask containing 70 ml of K1 and cultured at 27° C. for 2–3 days. One ml of the culture medium was inoculated in another flask containing the same culture medium as the above and cultured for 48–72 hours. Further, 140 ml of this culture medium was inoculated into a 30 liters jar fermenter containing 18 liters of the same medium as the above and cultured by aeration and stirring under the following conditions at 27° C. for 5–8 days:

aeration rate: 18 liters/minute and stirring rate: 350 rpm.

After the culture, mycelium was separated by centrifugation and extracted with acetone overnight. To the aqueous solution obtained by evaporating acetone from the extract solution under vacuum, the same volume of butanol was added followed by 3 times extraction. The butanol layer was condensed under vacuum to yield about 30.4 g of crude extract, which was dissolved in 80 ml of methanol. Then, 240 ml of chloroform was added thereto, and mixed with 50 g of silica gel, which was applied on a silica gel column (8×18 cm) saturated with chloroform/methanol (3:1) and contaminants were removed with chloroform/methanol (2:1) and chloroform/methanol (1:1). Then, active substance was eluted with chloroform/methanol (1:2) and chloroform/methanol (1:3). The eluted solution was condensed under vacuum to yield about 7.73 g of crude extract, which was dissolved in acetonitrile/0.1% diethylamine-formic acid (pH 4) (40:60) and so that the concentration thereof would be 100 mg/ml and centrifuged to separate culture supernatant. Then, this was fractionated further by HPLC. Firstly, this was separated using Senshu pak ODS (20φ×250 mm) and acetonitrile-0.1% diethylamine-formic acid (pH 4) (40:60), (50:50), (60:40) as stepwise eluent at flowing rate of 10 ml/min. Then, refractionation was carried out using Capcell pak ODS (20φ×250 mm) using acetonitrile 0.1% diethylamine-formic acid (pH 4) (37.5:62.5), (42.5:57.5), (50:50) as stepwise eluent to yield each component. Each liposidomycins fraction obtained as the above was condensed under vacuum to remove acetonitrile. Water was added to each fraction for desalting, which was applied on MCI GEL (1×5 cm), washed with sufficient amount of water, eluted with 70% acetone, condensed under vacuum and freeze-dried to yield white powder of liposidomycins as an active substance. Under these conditions, liposidomycins C-(III) (51.8 mg) and M-(III) (34.1 mg) were obtained as main components).

[Biological Activity]

(1) Antibacterial Activity

Methanol solution of each tested substance with specific concentration was sunk on a paper disk with diameter of 8 mm (Thick, Toyo-roshi) and dried, which was placed on a plate of each bacterium. After culture under the conditions suitable for each bacterium, the diameter of cell growth was measured, The results are shown in Table 4, 5 and 6.

TABLE 5

| Compound | Sample | The diameter of cell growth inhibition zone against M. Phlei (2 μg/disc, mm) |
|---|---|---|
| (I)Type I (having both sulfate group and 3-methylglutaric acid group) | | |
| Liposidomycins | A | 0 ⎤ |
| | B | 0 ⎥ known substances |
| | C | 0 ⎥ |
| | Z | 0 ⎦ |
| | L | 14.08 |
| | M | 16.86 |
| | K | 13.15 |
| | N | 11.59 |
| (II) Type II (having sulfate group but not 3-methylglutaric acid group) | | |
| | A-(II) | 0 |
| (III) Type III (having 3-methylglutaric acid group but not sulfate group) | | |
| | X-(III) | 13.23 |
| | Y-(III) | 0 |
| | Z-(III) | 13.74 |
| | C-(III) | 16.21 |
| | V-(III) | — |
| | A-(III) | 11.62 |
| | G-(III) | 16.68 |
| | M-(III) | 15.49 |
| | K-(III) | 12.27 |
| | N-(III) | 11.15 |
| (IV) Type IV (having neither sulfate group or 3-methylglutaric acid group) | | |
| | A-(IV) | 19.90 |

— represents "not assayed"

TABLE 6

| Compound | A | A-(II) | A-(III) | A-(IV) |
|---|---|---|---|---|
| Sulfate group | o | o | x | x |
| 3-Methylglutaric acid group | o | x | o | x |
| The diameter of cell growth inhibition zone against M. phlei (2 μg/disc, mm) | 0 | 0 | 14.3⁻ | 23.4 |

(2) Inhibitory Activity on Peptidoglycan Synthesis

Crude enzyme and substrate UDP-MurNAc-pentapeptide were prepared from *Escherichia coli* and *Bacillus subtilis*

TABLE 4

| Bacterium | Compound | | | | | | | | | | | |
|---|---|---|---|---|---|---|---|---|---|---|---|---|
| | A | A(III) | C | C(III) | M | M(III) | K | K(III) | N | N(III) | Z | Z(III) |
| *Escherichia coli* AB 1157 | 0 | 0 | 0 | 0 | 0 | 0 | 0 | 0 | 0 | 0 | 0 | 0 |
| *Escherichia coli* BE 1186 | + | 17.8 | 0 | 14.3 | 0 | (+) | (+) | 13.5 | 0 | 15.2 | — | 18.8 |
| *Staphylococcus aureus* IFO 12732 | 0 | 0 | 0 | 0 | 0 | 0 | 0 | 0 | 0 | 0 | 0 | 0 |
| *Bacillus subtilis* IFO 3513 | 0 | 21.0 | 0 | 17.8 (23.7) | 9.7 (13.0) | 14.8 | (+) | 13.0 | (+) | 12.9 | 0 | 22.2 |
| *Mycobacterium phlei* IFO 3158 | 18.9 | 24.8 | 22.1 | 30.3 | 27.2 | 25.7 | 28.6 | 23.3 | 23.1 | 20.8 | — | 26.3 |
| *Candida albicans* IFO 5994 | 0 | 0 | 0 | 0 | 0 | 0 | 0 | 0 | 0 | 0 | 0 | 0 |

(20 μg/disc, the diameter of cell growth inhibition zone: mm)

( ) represents partial inhibition

— represents "not assayed"

respectively according to a reference (J. Biol. Chem., 243, 3180 (1968)). Enzymatic reaction was carried out by mixing 5 μl of 1M Tris-HCl (pH 7.5), 10 μl of 0.1M $MgCl_2$, 5 μl of 2 mM UDP-MurNAc-pentapeptide, 5 μl of enzyme solution (15 mg/ml protein concentration), 5 μl of sample, 5 μl of UDP-[U-$^3$H]GlcNAc (10 μCi/ml, 25.8 Ci/mmol., Du'pont) and 15 μl of water at 37° C. for 60 minutes and 1 ml of reaction mixture was added to 5% TCA. After ice-cooling, it was trapped on a GF/C glass filter(2.4 cm, Whatman). And after adding scintillator thereto, radiation thereof was counted. Inhibitory % was calculated by comparing the count of control. The results are shown in Table 7.

(3) Cytotoxicity Test

BALB/3T3 cells (100 μl) were inoculated into 10% FBS added DMEM medium (Gibco) in 96 well plate so as to be 1×10$^5$ cells/ml under 5% $CO_2$ at 37° C., which was cultured overnight. The test substance dissolved in methanol was added thereto, which was cultured for more 3 days and further kept cultured for 4 hours after adding 10 μl of 2.5 mg/ml MTT reagent (Sigma). After removing supernatant, 100 μl of DMSO was added thereto and kept it overnight. The absorbance thereof at 540 nm was determined to detect viable cells. The results are shown in Table 8.

TABLE 7

| Compound | A | A-(II) | A-(III) | A-(IV) | TM |
|---|---|---|---|---|---|
| Inhibitory activity on peptidoglycan synthesis (0.1 μg/ml) | 95 | 90 | 96 | 94 | 10 |

TM: Tunicamycin

TABLE 8

| Compound | A | A-(II) | A-(III) | A-(IV) | TM |
|---|---|---|---|---|---|
| Cytotoxicity against BALB/3T3 ($IC_{50}$, μg/ml) | >25 | >25 | >25 | >25 | 0.05 |

TM: Tunicamycin

INDUSTRIAL UTILITY

As described specifically, the present invention is to provide a novel antibiotic liposidomycins and salts thereof and a method of producing liposidomycins. Antibiotic liposidomycins of the present invention has quite low cytotoxicity but a strong antibacterial activity by inhibiting peptidoglycan synthesis.

Reference to Microorganism

1. *Streptomyces* sp. SN-1061M

Deposit authority: National Institute of Bioscience and Human-Technology Agency of Industrial Science and Technology Ministry of International Trade and Industry
Address: 1-3, Higashi 1-chome, Tsukuba-shi, Ibaraki-ken 305, Japan
Date of Deposit: Jan. 28, 1997
Deposit No.: FERM BP-5800

What is claimed:

1. A microorganism which is *Streptomyces* species SN-1061M (FERM BP-5800).

* * * * *